US008831271B2

(12) United States Patent
Sese et al.

(10) Patent No.: US 8,831,271 B2
(45) Date of Patent: Sep. 9, 2014

(54) SUBGRAPH DETECTION DEVICE, SUBGRAPH DETECTION METHOD, PROGRAM, DATA STRUCTURE OF DATA, AND INFORMATION RECORDING MEDIUM

(75) Inventors: Jun Sese, Taito-ku (JP); Mio Seki, Kita-ku (JP)

(73) Assignee: Ochanomizu University, Tokyo (JP)

( * ) Notice: Subject to any disclaimer, the term of this patent is extended or adjusted under 35 U.S.C. 154(b) by 650 days.

(21) Appl. No.: 13/122,623

(22) PCT Filed: Oct. 7, 2009

(86) PCT No.: PCT/JP2009/067476
§ 371 (c)(1),
(2), (4) Date: Apr. 5, 2011

(87) PCT Pub. No.: WO2010/041678
PCT Pub. Date: Apr. 15, 2010

(65) Prior Publication Data
US 2011/0182479 A1 Jul. 28, 2011

(30) Foreign Application Priority Data
Oct. 7, 2008 (JP) ................................. 2008-260827

(51) Int. Cl.
*G06K 9/00* (2006.01)
*G06T 11/20* (2006.01)
*G06F 19/26* (2011.01)
*G06F 17/30* (2006.01)
*G06F 19/12* (2011.01)

(52) U.S. Cl.
CPC .......... *G06F 17/30958* (2013.01); *G06F 19/12* (2013.01); *G06F 19/26* (2013.01); *G06F 17/30961* (2013.01)
USPC .......................................... 382/100; 345/440

(58) Field of Classification Search
None
See application file for complete search history.

(56) References Cited

U.S. PATENT DOCUMENTS 5,123,057 A * 6/1992 Verly et al. .................... 382/156
5,278,951 A * 1/1994 Camacho et al. ............. 345/440

(Continued)

FOREIGN PATENT DOCUMENTS

JP 2000-123041 A 4/2000
JP 2002-091991 A 3/2002

(Continued)

OTHER PUBLICATIONS

Freuder ("A sufficient condition for backtrack free search", 1982).*

(Continued)

*Primary Examiner* — Avinash J Yentrapati
(74) *Attorney, Agent, or Firm* — Sughrue Mion, PLLC

(57) ABSTRACT

To provide a detection device capable of, e.g., obtaining a list of genes whose expressions are commonly changed in response to administration of a specific drug or drugs, based on consideration of relationship (e.g., interacting relationship among genes) among genes, a list of proteins whose expressions are commonly changed in response to administration of a specific drug or drugs, based on consideration of relationship (e.g., interacting relationship among proteins) among proteins, and a list of users who purchased an identical product or products, based on consideration of relationship (e.g., friendship) among users, and so forth. A graph data obtaining unit (20) obtains graph data indicating a graph including a plurality of vertexes. A vertex data obtaining unit (22) obtains vertex data that correlates an information item to a vertex. Based on the graph data and the vertex data, a subgraph detection unit (24) detects a subgraph that is a subgraph of the graph in which information items correlated to the respective vertexes in the subgraph have predetermined relationship.

16 Claims, 8 Drawing Sheets

(56) References Cited

U.S. PATENT DOCUMENTS

| | | | |
|---|---|---|---|
| 5,450,535 A * | 9/1995 | North | 345/440 |
| 5,905,507 A * | 5/1999 | Rossignac et al. | 345/440 |
| 6,728,205 B1 * | 4/2004 | Finn et al. | 370/217 |
| 7,102,641 B2 * | 9/2006 | Hudson, Jr. | 345/440 |
| 7,614,037 B2 * | 11/2009 | Gavrilov | 717/105 |
| 8,249,231 B2 * | 8/2012 | Chakraborty et al. | 379/112.01 |
| 2002/0163518 A1 * | 11/2002 | Rising et al. | 345/440 |
| 2007/0100680 A1 * | 5/2007 | Kumar et al. | 705/10 |
| 2007/0244747 A1 | 10/2007 | Nikovski | |
| 2008/0218518 A1 * | 9/2008 | Zhou et al. | 345/440 |

FOREIGN PATENT DOCUMENTS

| | | |
|---|---|---|
| JP | 2004-220227 A | 8/2004 |
| JP | 2004-272627 A | 9/2004 |
| JP | 2007-287139 A | 11/2007 |

OTHER PUBLICATIONS

International Preliminary Report on Patentability in counterpart PCT/JP2009/067476 dated May 26, 2011.

Office Action issued in corresponding Japanese Patent Application No. 2010-532936 dated Aug. 6, 2013.

Office Action, dated Mar. 18, 2014, issued by the Japanese Patent Office, in counterpart Application No. 2010-532936.

* cited by examiner

| v | I(v) |
|---|---|
| $v_1$ | $i_1$(DRUG A), $i_2$(DRUG B), $i_3$(DRUG C), $i_4$(DRUG D) |
| $v_2$ | $i_1$, $i_5$(DRUG E) |
| $v_3$ | $i_1$, $i_2$, $i_4$ |
| $v_4$ | $i_1$, $i_2$, $i_5$ |
| $v_5$ | $i_1$, $i_3$, $i_4$ |
| $v_6$ | $i_1$, $i_3$, $i_5$ |

| v | I(v) |
|---|---|
| $v_1$ | $i_1$(APPLE), $i_2$(MANDARIN), $i_3$(GRAPE), $i_4$(PEAR) |
| $v_2$ | $i_1$, $i_5$(MELON) |
| $v_3$ | $i_1$, $i_2$, $i_4$ |
| $v_4$ | $i_1$, $i_2$, $i_5$ |
| $v_5$ | $i_1$, $i_3$, $i_4$ |
| $v_6$ | $i_1$, $i_3$, $i_5$ |

FIG.8

| v | P (v) |
|---|---|
| $v_1$ | $\{i_1, i_2, i_3, i_4\}$ |
| $v_2$ | $\{i_1, i_5\}$ |
| $v_3$ | $\{i_1, i_2, i_4\}$ |
| $v_4$ | $\{i_1, i_2\}\{i_1, i_2, i_5\}$ |
| $v_5$ | $\{i_1, i_3\}$ |
| $v_6$ | $\{i_1, i_3\}$ |

SUBGRAPH DETECTION DEVICE, SUBGRAPH DETECTION METHOD, PROGRAM, DATA STRUCTURE OF DATA, AND INFORMATION RECORDING MEDIUM

CROSS REFERENCE TO RELATED APPLICATIONS

This application is a National Stage of International Application No. PCT/JP2009/067476 filed on Oct. 7, 2009, which claims priority from Japanese Patent Application No. 2008-260827, filed on Oct. 7, 2008, the contents of all of which are incorporated herein by reference in their entirety.

TECHNICAL FIELD

The present invention relates to a subgraph detection device, a subgraph detection method, a program, a data structure of data, and an information recording medium.

BACKGROUND ART

For example, lists of users who purchased or did not purchase a specific product or products have been obtained based on data that correlates a purchased product list to each of a plurality of users. Further, for example, lists of documents with a keyword or key words set thereon have been obtained based on data that correlates a key word list to each of a plurality of documents.

For example, the patent document 1 below describes specification of a user who did not purchase a specific product or products (e.g., a frequently purchased product or products), based on purchased product lists of a plurality of users.

RELATED ART DOCUMENT

Patent Document

Patent Document 1: Japanese Patent Laid-open Publication No. 2007-287139

DISCLOSURE OF THE INVENTION

Problems to be Solved by the Invention

Conventionally, it has not been possible, for example, to obtain a list of users who purchased an identical product or products, based on consideration of relationship (e.g., friendship) among users. Further, it has not been possible, for example, to obtain a list of documents with the same keyword or keywords set thereon, based on consideration of relationship (reference relationship) among documents.

Here, if a list of genes that commonly change expressions thereof in response to administration of a specific drug or drugs can be obtained based on consideration of gene relationship, it will be possible to obtain useful information in view of drug discovery research. For example, if such a list can be obtained based on consideration of relationship (interaction relationship among genes) among genes having mutual influence on expressions thereof or genes that are expressed at the same time, it will be possible to obtain useful information in, e.g., narrowing down drug discovery targets. However, it has not been possible so far to obtain a list of genes that commonly change expression thereof in response to administration of a specific drug or drugs, based on consideration of gene relationship.

Further, if a list of proteins that commonly change expression thereof in response to administration of a specific drug or drugs can be obtained based on consideration of protein relationship, it will be possible to obtain useful information in view of drug discovery research. For example, if such a list can be obtained based on consideration of relationship (interaction relationship among proteins) among proteins that are bound to each other to be a composite, it will be possible to obtain useful information in, e.g., narrowing down drug discovery targets. However, it has not been possible so far to obtain a list of proteins that commonly change expression thereof in response to administration of a specific drug or drugs, based on consideration of protein relationship.

The present invention has been conceived in view of the above, and an object thereof is to provide a subgraph detection device, a subgraph detection method, a program, a data structure of data, and an information recording medium capable of obtaining, e.g., a list of genes that commonly change expression thereof in response to administration of a specific drug or drugs, based on consideration of gene relationship (e.g., interacting relationship among genes), a list of proteins that commonly change expression thereof in response to administration of a specific drug or drugs, based on consideration of protein relationship (e.g., interacting relationship among proteins), a list of users who purchased an identical product or products, based on consideration of relationship (e.g., friendship) among users, and a list of documents with the same key word or key words set thereon, based on consideration of relationship (reference relationship) among documents.

Means for Solving the Problems

In order to solve the above described problems, a subgraph detection device according to the present invention comprises a graph data obtaining unit for obtaining graph data indicating a graph including a plurality of vertexes and one or more edges; a vertex data obtaining unit for obtaining vertex data that correlates an information item to the vertex; and a subgraph detection unit for detecting, based on the graph data and the vertex data, a subgraph being a subgraph of the graph in which the information items correlated to the respective vertexes in the subgraph have a predetermined relationship.

A subgraph detection method according to the present invention comprises a graph data obtaining step of obtaining graph data indicating a graph including a plurality of vertexes and one or more edges; a vertex data obtaining step of obtaining vertex data that correlates an information item to the vertex; and a subgraph detection step of detecting, based on the graph data and the vertex data, a subgraph being a subgraph of the graph in which the information items correlated to the respective vertexes in the subgraph have a predetermined relationship.

A program according to the present invention causes a computer to function as a graph data obtaining unit for obtaining graph data indicating a graph including a plurality of vertexes and one or more edges; a vertex data obtaining unit for obtaining vertex data that correlates an information item to the vertex; and a subgraph detection unit for detecting, based on the graph data and the vertex data, a subgraph being a subgraph of the graph in which the information items correlated to the respective vertexes in the subgraph have a predetermined relationship.

An information recording medium according to the present invention is a computer readable information recording medium recording the above described program.

A data structure according to the present invention comprises graph data indicating a graph including a plurality of vertexes and one or more edges and vertex data that correlates an information item to the vertex. An information recording medium according to the present invention records data comprising graph data indicating a graph including a plurality of vertexes and one or more edges and vertex data that correlates an information item to the vertex.

The present invention relates to a technique for detecting a subgraph of a graph including a plurality of vertexes and one or more edges. In the present invention, graph data indicating the graph is obtained. For example, graph data indicating a graph in which each vertex corresponds to each gene and each edge (link) shows a relationship between genes is obtained. Note that "a relationship between genes" means, for example, a relationship between genes having mutual influence on expressions thereof (interacting relationship among genes) or a relationship between genes that are expressed at the same time. Further, for example, graph data indicating a graph in which each vertex corresponds to a protein and each edge (link) shows a relationship between proteins is obtained. Note that "a relationship between proteins" means, for example, a relationship between proteins that are bound to one another to be a composite (interacting relationship among proteins). Still further, for example, graph data indicating a graph in which each vertex corresponds to each user and each edge (link) shows friendship between users is obtained. Note that graph data is expressed as, e.g., an adjacent list or an adjacent matrix. In the present invention, vertex data that correlates information to the vertex is obtained, and a subgraph in which information items correlated to the respective vertexes in the subgraph have a predetermined relationship is detected based on the graph data and the vertex data. According to the present invention, a subgraph is detected based on the graph data and the vertex data. As a result, it is possible to obtain, e.g., a list of genes that commonly change expression thereof in response to administration of a specific drug or drugs, based on consideration of relationship among genes (e.g., an interacting relationship among genes). Further, it is possible to obtain, e.g., a list of proteins that commonly change expression thereof in response to administration of a specific drug or drugs, based on consideration of relationship among proteins (e.g., an interacting relationship among proteins). Still further, it is possible to obtain, e.g., a list of users who purchased an identical product or products, based on consideration of relationship among user (e.g., friendship).

According to one aspect of the present invention, the information item may indicate an element set including at least one kind of element, and the subgraph detection unit may carry out detection of a subgraph being a subgraph of the graph in which a product set of the element sets correlated to the respective vertexes in the subgraph includes an N (N≥1) or larger number of kinds of elements. For example, when each vertex corresponds to each gene and each element set corresponds to a drug or drugs that changes/change expression of a gene, it is possible to obtain a list of genes that commonly change expression thereof in response to administration of a specific drug or drugs, based on consideration of relationship among genes (e.g., an interacting relationship among genes). Further, e.g., when each vertex corresponds to each protein and each element set corresponds to a drug or drugs that changes/change expression of a protein, it is possible to obtain a list of proteins that commonly change expression thereof in response to administration of a specific drug or drugs, based on consideration of relationship among proteins (e.g., an interacting relationship among genes). Still further, when each vertex corresponds to each user and each element set corresponds to a product purchased by a user, it is possible to obtain a list of users who purchased an identical product or products, based on consideration of relationship among users (e.g., friendship).

According to one aspect of the present invention, the subgraph detection unit may include a determination unit, while making respective nodes of a search tree as a determination target in a search order according to a depth-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, for carrying out determination to see whether or not a product set of element sets correlated to the respective vertexes in the vertex set of the node being the determination target includes the N or larger number of kinds of elements, and a unit for carrying out the detection, based on a result of determination by the determination unit, and when a product set of element sets correlated to respective vertexes in a vertex set of a first node in the search tree is included in a product set of element sets correlated to respective vertexes in a vertex set of a second node that is a node having a vertex set including an end vertex that is the same as an end vertex in the vertex set of the first node and that is a node before the first node in the search order, the determination unit may not carry out the determination with respect to a vertex set of a descendant node of the first node as a determination target.

According to one aspect of the present invention, the subgraph detection unit may include a unit for storing, when the determination is carried out, the product set of the element sets correlated to the respective vertexes in the vertex set of the node being the determination target as a reference set in a reference set storage unit so as to be correlated to an end vertex in the vertex set of the node being the determination target, and when the product set of the element sets correlated to the respective vertexes in the vertex set of the first node is included in a reference set that is stored in the reference set storage unit so as to be correlated to the end vertex in the vertex set of the first node, the determination unit may not carry out the determination with respect to the vertex set of the descendant node of the first node as the determination target.

According to one aspect of the present invention, the subgraph detection unit may include a determination unit, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, for carrying out determination to see whether or not a product set of element sets correlated to the respective vertexes in the vertex set of the node being the determination target includes the N or larger number of kinds of elements, and a unit for carrying out the detection, based on a result of determination by the determination unit, and when a product set of element sets correlated to respective vertexes in a vertex set of a first node in the search tree is included in a product set of element sets correlated to respective vertexes in a vertex set of a second node that is a node having a vertex set including an end vertex that is the same as an end vertex in the vertex set of the first node and that is a node having a vertex set including the vertex set of the first node, the determination unit may not carry out the determination with respect to a vertex set of a descendant node of the first node as a determination target.

According to one aspect of the present invention, the subgraph detection unit may include a determination unit, while making respective nodes of a search tree as a determination target in a search order according to a depth-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, for carrying out determination to see whether or not a product set of element sets correlated to the respective vertexes in the vertex set of the node being the determination target includes the N or larger number of kinds of elements, and a unit for carrying out the detection, based on a result of determination by the determination unit, and when a vertex set of a third node in the search tree includes only one vertex, and an element set correlated to the vertex is included in a product set of element sets correlated to respective vertexes in a vertex set of a fourth node that is a node having a vertex set including the vertex as an end vertex and that is a node before the third node in the search order, the determination unit may not carry out the determination with respect to a vertex set of a descendant node of the third node as the determination target.

According to one aspect of the present invention, the subgraph detection unit may include a unit for storing, when the determination is carried out, the product set of the element sets correlated to the respective vertexes in the vertex set of the node being the determination target as a reference set in a reference set storage unit so as to be correlated to an end vertex in the vertex set of the node being the determination target, and when the vertex set of the third node includes only one vertex and the element set correlated to the vertex is included in a reference set that is stored in the reference set storage unit so as to be correlated to the vertex, the determination unit may not carry out the determination with respect to the vertex set of the descendant node of the third node as the determination target.

According to one aspect of the present invention, the subgraph detection unit may include a determination unit, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, for carrying out determination to see whether or not a product set of element sets correlated to the respective vertexes in the vertex set of the node being the determination target includes the N or larger number of kinds of elements, and a unit for carrying out the detection, based on a result of determination by the determination unit, and when a vertex set of a third node in the search tree includes only one vertex, and an element set correlated to the vertex is included in a product set of element sets correlated to respective vertexes in a vertex set of a fourth node that is a node having a vertex set including the vertex as an end vertex, the determination unit may not carry out the determination with respect to a vertex set of a descendant node of the third node as the determination target.

According to one aspect of the present invention, the subgraph detection unit may include a determination unit, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, for carrying out determination to see whether or not a product set of element sets correlated to the respective vertexes in the vertex set of the node being the determination target includes the N or larger number of kinds of elements, and a unit for carrying out the detection, based on a result of determination by the determination unit, and when a product set of element sets correlated to respective vertexes in a vertex set of the node does not include the N or large number of kinds of elements, the determination unit may not carryout the determination with respect to a vertex set of a descendant node of the node as the determination target.

BRIEF DESCRIPTION OF THE DRAWINGS

FIG. 8 is a diagram showing one example of content of a reference set table;

BEST MODE FOR CARRYING OUT THE INVENTION

In the following, an embodiment of the present invention will be described with reference to the accompanying drawings.

[1. Structure Of Subgraph Detection System]

Figure 1:
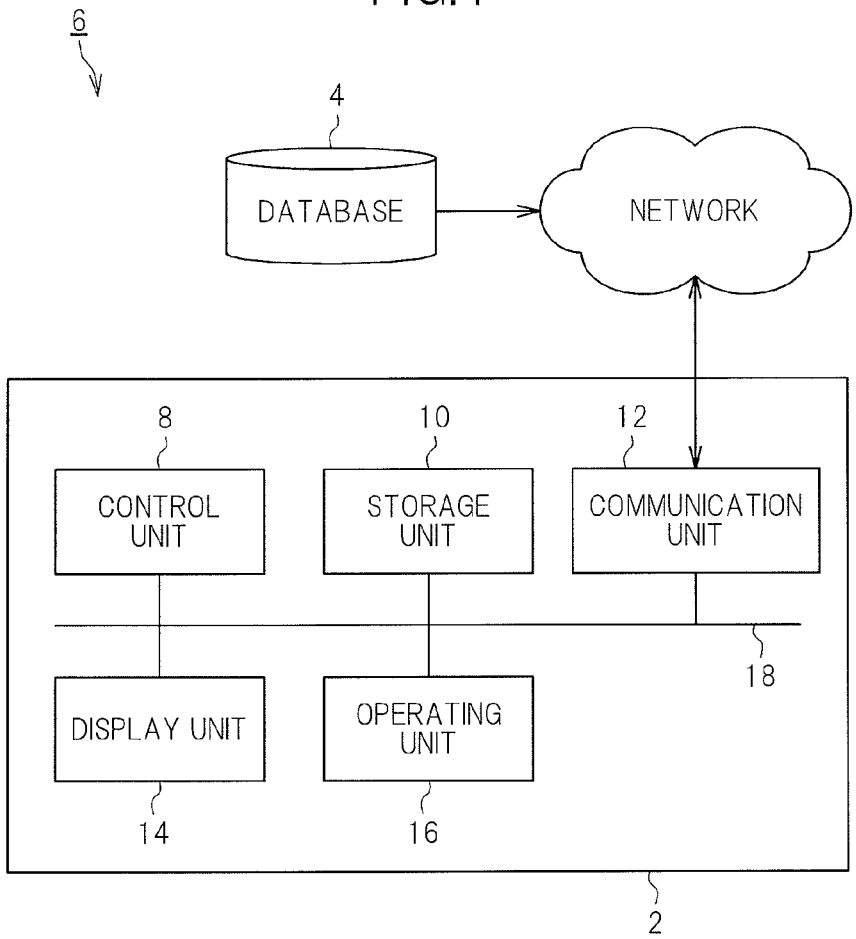
FIG. 1 is a diagram showing a structure of a subgraph detection system including a subgraph detection device according to an embodiment of the present invention.

FIG. 1 is a diagram showing a structure of a subgraph detection system 6 including a subgraph detection device 2 according to an embodiment of the present invention. As shown in the diagram, the subgraph detection system 6 comprises a subgraph detection device 2 and a database 4, which can communicate to each other via a network.

[2. Hardware Structure Of Subgraph Detection Device]

The subgraph detection device 2 is e.g., a personal computer. As shown in FIG. 1, the subgraph detection device 2 comprises a control unit 8, a storage unit 10, a communication unit 12, a display unit 14, an operating unit 16, which are connected to one another for communication via a bus 18.

The control unit 8 carries out various kinds of information processes according to a program stored in the storage unit 10. While the control unit 8 carries out a process as a personal computer, a process according to the present invention will be mainly described below. Specific contents of the processes carried out by the control unit 8 will be described later.

The storage unit 10 includes a main memory and a nonvolatile memory. The nonvolatile memory stores a program carried out by the control unit 8. The program is downloaded from, e.g., a program distribution device via a network to be stored in the nonvolatile memory. Alternatively, the program may be copied from a computer readable information recording medium, such as, e.g., an optical disk or a memory card, to be stored in the nonvolatile memory. A program read from the nonvolatile memory and various data necessary in a process by the control unit 8 are written into the main memory when necessary.

The communication unit 12 includes a network interface card, and outputs, e.g., data having arrived to the control unit 8 via a network. The display unit 14 includes, e.g., a monitor, and shows the data input from the control unit 8. The operating unit 16 includes a keyboard and/or a mouse, and outputs data indicating content of a user operation to the control unit 8.

[3. Database]

The database 4 is stored in, e.g., a hard disk (an information recording medium) in a database server. Alternatively, the database may be stored in the nonvolatile memory (an information recording medium) of the subgraph detection device 2.

The database 4 stores graph data indicating a graph including a plurality of vertexes and one or more links (edges). Note that although a "vertex" of a graph may be referred to also as a "node", the term "vertex" is used here in order to discriminate from a node of a tree to be described later (see FIG. 7).

Figure 2:
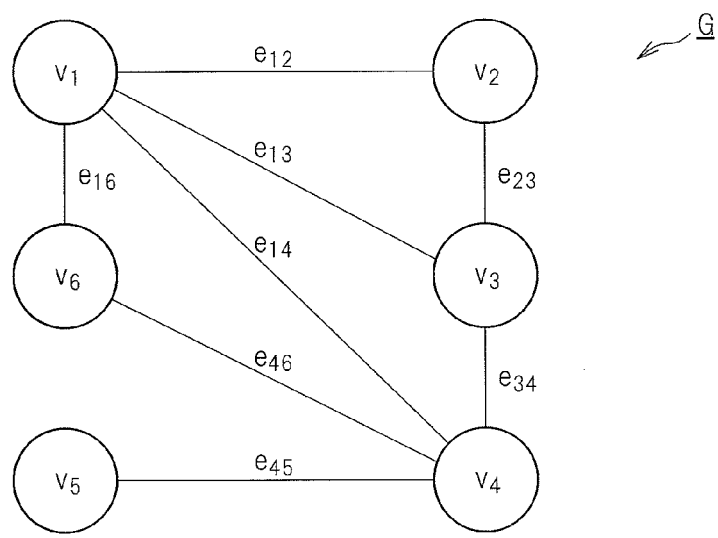
FIG. 2 is a diagram showing one example of a graph indicated by graph data.

The graph data is data describing, e.g., an adjacent list and/or an adjacent matrix. FIG. 2 is a diagram showing one example of the graph data. The graph G shown in FIG. 2 includes six vertexes v and links e each connecting one vertex v and another vertex v. That is, the graph G shown in FIG. 2 includes 6 vertexes $\{v_1, v_2, v_3, v_4, v_5, v_6\}$ and eight links $\{e_{12}, e_{13}, e_{14}, e_{16}, e_{23}, e_{34}, e_{45}, e_{46}\}$.

In this embodiment, the graph G shown in FIG. 2, in which each vertex v corresponds to each gene, shows relationship among the genes. In the specification, "relationship among the genes" refers to, e.g., relationship among genes having mutual influence on the expressions thereof (interacting relationship among genes) and/or relationship among genes that are expressed at the same time. Specifically, the link $e_{ij}$ connecting a vertex $v_i$ and a vertex $v_j$ indicates that the gene corresponding to the vertex $v_i$ has a relationship with the gene corresponding to the vertex $v_j$. For example, in the graph G shown in FIG. 2, the link $e_{12}$ connects the vertex $v_1$ and the vertex $v_2$, and this means that the gene corresponding to the vertex $v_1$ has a relationship with the gene corresponding to the vertex $v_2$. Further, in the graph G shown in FIG. 2, the vertex $v_1$ is connected via the link $e_{14}$ to the vertex $v_4$, which is further connected via the link $e_{45}$ to the vertex $v_5$. This means that the gene corresponding to the vertex $v_1$ has an indirect relationship with the gene corresponding to the vertex $v_5$ via the gene corresponding to the vertex $v_4$.

Figures 3, 4:
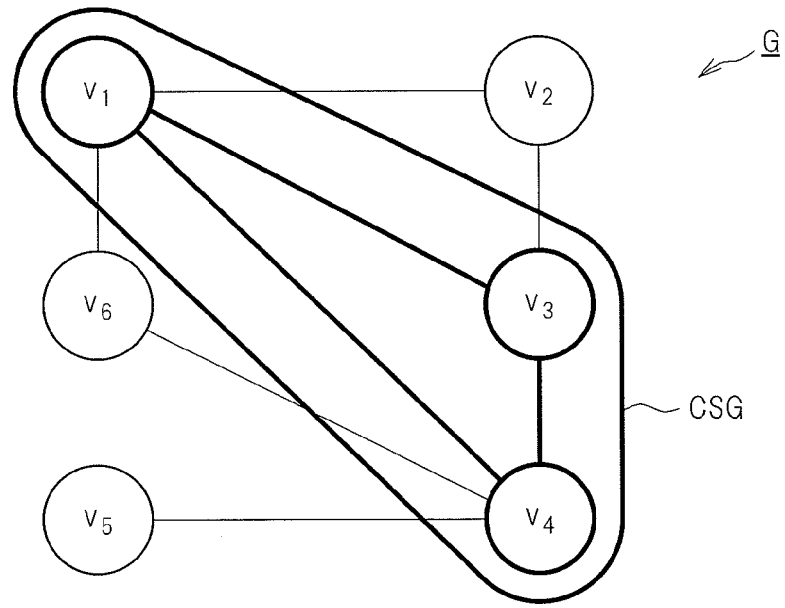
FIG. 3 is a diagram showing one example of content of vertex data.
FIG. 4 is a diagram showing one example of a subgraph CSG.

In addition, the database 4 stores vertex data that correlates information to each of the vertexes v in the graph G. FIG. 3 is a diagram showing one example of the vertex data. The vertex data shown in FIG. 3 is a table that correlates a vertex v to an item set I(v) including at least one kind of item i (an element). In this embodiment, each of the items $i_i$ included in the item set $I(v_i)$ corresponds to a drug that changes expression of the gene corresponding to the vertex $v_i$. In the example shown in FIG. 3, the item set $I(v_1)$ correlated to the vertex $v_1$ includes an item $i_1$ (drug A), an item $i_2$ (drug B), an item $i_3$ (drug C), and an item $i_4$ (drug D). This means that administration of the drug A, drug B, drug C, or drug D changes expression of the gene corresponding to the vertex $v_1$. Note that, for example, the item i may correspond to a factor other than a drug that changes expression of a gene.

Note that, in a subgraph CSG that is a part of the graph G, as shown in FIG. 4, the item sets $I(v_1)$, $I(v_3)$, $I(v_4)$ correlated to the respective vertexes $v_1$, $v_3$, $v_4$ included in the subgraph CSG each include a common item set $\{i_1, i_2\}$. This means that expression of the three genes having direct or indirect relationship to one another (three genes corresponding to the respective vertexes $v_1$, $v_3$, $v_4$) will change in response to administration of the common drugs $\{drug A, drug B\}$. In this case, it is inferred that it is highly likely that expression of the three genes will change in response to administration of the same or similar drug as the three genes have a direct or indirect relationship to one another and the expressions thereof are changed in response to administration of the common drug. If genes having a direct or indirect relationship to one another whose expressions are changed in response to administration of a common drug, such as these three genes, can be specified, that will be useful in, e.g., drug discovery research. For example, that will be useful in narrowing down genes to be a drug discovery target.

Regarding this point, in the subgraph detection device 2, a subgraph CSG that is a subgraph of the graph G in which item sets I(v) correlated to the respective vertexes v in the subgraph include a common item set is detected. As a result, genes having a direct or indirect relationship to one another whose expressions are changed in response to administration of a common drug can be detected.

Note that each of the vertexes v in the graph G may correspond to each protein, and each item $i_i$ in the vertex data may correspond to a drug that changes expression of the protein corresponding to a vertex $v_i$.

In this case, the graph G shown in FIG. 2 shows relationship among proteins in which the link $e_{ij}$ connecting a vertex $v_i$ and a vertex $v_j$ indicates that the protein corresponding to the vertex $v_i$ has a relationship with the protein corresponding to the vertex $v_j$. Note that "relationship among proteins" refers to, e.g., relationship among proteins that are bound to one another to be a composite (an interacting relationship among proteins). For example, in the graph G shown in FIG. 2, the link $e_{12}$ connects the vertex $v_1$ and the vertex $v_2$, and this means that the protein corresponding to the vertex $v_1$ has a relationship with the protein corresponding to the vertex $v_2$. Further, in the graph G shown in FIG. 2, the vertex $v_1$ is connected to the vertex $v_4$ via the link $e_{14}$ and the vertex $v_4$ is further connected to the vertex $v_5$ via the link $e_{45}$, and this means that the protein corresponding to the vertex $v_1$ has an indirect relationship with the protein corresponding to the vertex $v_5$ via the protein corresponding to the vertex $v_4$.

In this case, vertex data similar to that shown in FIG. 3 is stored in the database 4. Specifically, in the vertex data shown in FIG. 3, the item set $I(v_1)$ correlated to the vertex $v_1$ includes an item $i_1$ (drug A), an item $i_2$ (drug B), an item $i_3$ (drug C), and an item $i_4$ (drug D), and this means that administration of the drug A, drug B, drug C, or drug D changes expression of the protein corresponding to the vertex $v_1$. Note that, for example, the item may correspond to any factor (e.g., heat shock, nitrogen starvation condition, or the like) other than a drug that changes expression of a protein.

As described above (see FIG. 4), in the subgraph CSG that is a part of the graph G, the item sets $I(v_1)$, $I(v_3)$, $I(v_4)$ correlated to the respective vertexes $v_1$, $v_3$, $v_4$ included in the subgraph CSG each include a common item set $\{i_1, i_2\}$. This means that expressions of three proteins having a direct or indirect relationship to one another (three proteins corresponding to the respective vertexes $v_1$, $v_3$, $v_4$) are changed in response to administration of the common drug {drug A, drug B}. In this case, it is inferred that it is highly likely that the expressions of the three proteins will change in response to administration of the same or similar drug as the three proteins have a direct or indirect relationship to one another and expressions thereof are changed in response to administration of the common drug. If proteins having a direct or indirect relationship to one another whose expressions are changed in response to administration of a common drug, such as these three proteins, can be specified, that will be useful in drug discovery research. For example, that will be useful in narrowing down proteins to be a drug discovery target.

Regarding this point, as described above, in the subgraph detection device 2, a subgraph CSG that is a subgraph of the graph G in which the item sets I(v) correlated to the respective vertexes v in the subgraph each include a common item set is detected. As a result, when each of the vertexes v in the graph G corresponds to one protein and each item $i_i$ corresponds to a drug that changes expression of the protein corresponding to a vertex $v_i$, proteins having a direct or indirect relationship to one another whose expressions are changed in response to administration of a common drug can be detected.

Further, each of the vertexes v in the graph G may correspond to a user, and each item $i_i$ included in the vertex data may correspond to a product purchased by the user corresponding to a vertex $v_i$.

In this case, the graph G shown in FIG. 2 shows friendship among users, and the link $e_{ij}$ connecting a vertex $v_i$ and a vertex $v_j$ indicates that the user corresponding to the vertex $v_i$ has a relationship with the user corresponding to the vertex $v_j$. For example, in the graph G shown in FIG. 2, the link $e_{12}$ connects the vertex $v_1$ and the vertex $v_2$, and this means that the user corresponding to the vertex $v_1$ has friendship with the user corresponding to the vertex $v_2$. Further, in the graph G shown in FIG. 2, the vertex $v_1$ is connected to the vertex $v_4$ via the link $e_{14}$ and the vertex $v_4$ is further connected to the vertex $v_5$ via the link $e_{45}$, and this means that the user corresponding to the vertex $v_1$ have indirect friendship with the user corresponding to the vertex $v_5$ via the user corresponding to the vertex $v_4$.

Figures 5, 6:
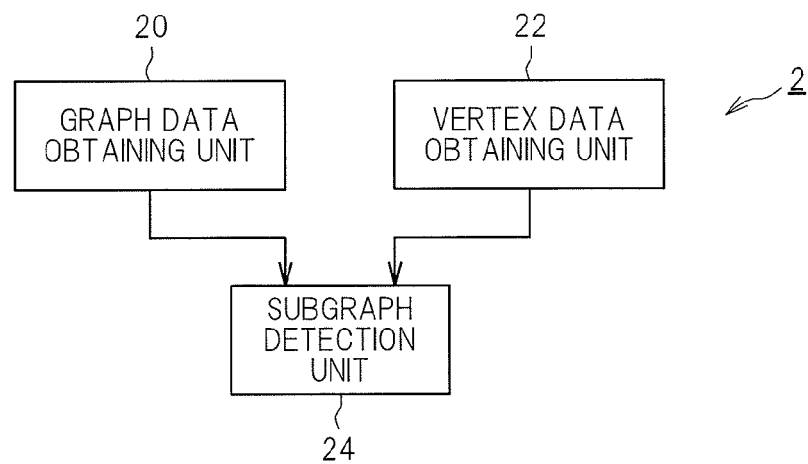
FIG. 5 is a diagram showing one example of content of vertex data.
FIG. 6 is a diagram showing functions realized in a subgraph detection device according to an embodiment of the present invention.

FIG. 5 shows one example of the vertex data for a case in which each item $i_i$ corresponds to a product purchased by the user corresponding to a vertex $v_i$. Specifically, in the example shown in FIG. 5, the item set $I(v_1)$ correlated to the vertex $v_1$ includes an item $i_1$ (apple), an item $i_2$ (mandarin), an item $i_3$ (grape), and an item $i_4$ (pear), and this means that the user corresponding to the vertex $v_1$ purchased an apple, a mandarin, a grape, and a pear. Note that although the items $i_1$ to $i_5$ correspond to similar kinds of products (fruits) here, the items $i_1$ to $i_5$ may correspond to different kinds of products.

As described above (see FIG. 4), in the subgraph CSG that is a part of the graph G, the item sets $I(v_1)$, $I(v_3)$, $I(v_4)$ correlated to the respective vertexes $v_1$, $v_3$, $v_4$ included in the subgraph CSG each include a common item set $\{i_1, i_2\}$. This means that the three users (three users corresponding to the respective vertexes $v_1$, $v_3$, $v_4$) having direct or indirect friendship to one another purchased common products {apple, mandarin}. In this case, it is inferred that it is highly likely that information relating to the common products {apple, mandarin} or other products related to the products is spreading through word of mouth communication among the three users corresponding to the respective vertexes $v_1$, $v_3$, $v_4$. If users having direct or indirect friendship to one another and having purchased a common product, such as these three users, can be specified, it will be possible to preferably narrow down the users to be targeted by an advertisement of a produce, so that an efficient advertisement of the product can be achieved.

Regarding this point, in the subgraph detection device 2, a subgraph CSG that is a subgraph of the graph G in which the respective item sets I(v) correlated to the respective vertexes v in the subgraph include a common item set is detected, and as a result, users having direct or indirect friendship to one another and having purchased a common product can be detected.

In the following, a technique for detecting a subgraph CSG in which item sets I(v) correlated to the respective vertexes v include a common item set will be described. Note that a subgraph CSG in which item sets I(v) correlated to the respective vertexes v include a common item set will be hereinafter referred to as a common subgraph CSG.

[4. Functional Block]

FIG. 6 is a functional block diagram mainly showing the functions according to the present invention among those realized in the subgraph detection device 2. As shown in the diagram, the subgraph detection device 2 functionally comprises a graph data obtaining unit 20, a vertex data obtaining unit 22, and a subgraph detection unit 24, which are realized by the control unit 8 operating according to the above described program read from the storage unit 10.

[4-1. Graph Data Obtaining Unit]

The graph data obtaining unit 20 is realized mainly using, e.g., the control unit 8 and the communication unit 12. The graph data obtaining unit 20 obtains graph data indicating a graph including a plurality of vertexes. In this embodiment, the graph data obtaining unit 20 reads, and thereby obtains, graph data on the graph G, such as is shown in, e.g., FIG. 2, from the database 4.

[4-2. Vertex Data Obtaining Unit]

The vertex data obtaining unit 22 is realized mainly using, e.g., the control unit 8 and the communication unit 12. The vertex data obtaining unit 22 obtains vertex data that correlates information to each of the plurality of vertexes included in the graph. Note that "information" here means information other than connection relationship information among the vertexes in the graph G. Specifically, for example, for a vertex corresponding to a gene, the above mentioned "information" means, e.g., information relating to a gene, and "information relating to a gene" means information indicating a drug that changes expression of a gene. Further, for example, for a vertex corresponding to a protein, the above mentioned "information" means information relating to a protein, and "information relating to a protein" means information indicating a drug that changes expression of a protein. Still further, for example, for a vertex corresponding to a user, the above mentioned "information" means information relating to a user, and "information relating to a user" means information indicating user attribute or a product purchased by a user. In this embodiment, the vertex data obtaining unit 22 reads, and thereby obtains, vertex data, such as is shown in, e.g., FIG. 3 or 5, from the database 4.

[4-3. Subgraph Detection Unit]

The subgraph detection unit 24 is realized mainly using, e.g., the control unit 8, and detects a subgraph, based on the graph data and the vertex data, the subgraph being a subgraph of a graph in which information items correlated to the respective vertexes in the subgraph have a predetermined relationship. In this embodiment, the subgraph detection unit 24 detects a common subgraph CSG that is a subgraph of the graph G in which the product set of the item sets I(v) correlated to the respective vertexes v in the subgraph includes an N (N being a positive integer) or larger number of kinds of items (products). Specifically, for example, a common subgraph CSG including a plurality of vertexes v corresponding to "a plurality of genes whose expressions are commonly changed in response to administration of an N or larger number of kinds of common drugs" is detected. Further, for example, a common subgraph CSG including a plurality of vertexes v corresponding to "a plurality of proteins whose expressions are commonly changed in response to administration of an N or larger number of kinds of common drugs" is detected. Still further, for example, a common subgraph CSG including "a plurality of vertexes v corresponding to a plurality of users having purchased an N or larger number of kinds of common products" is detected.

Note that, in this embodiment, a common subgraph CSG that is closed (hereinafter referred to as a closed common subgraph CCSG), in particular, is detected. A closed common subgraph CCSG is a common subgraph CSG in which addition of any vertex v adjacent to a vertex v included in the common subgraph CSG changes the common item set thereof.

In the following, a specific example of a closed common subgraph CCSG will be described based on an assumption that a subgraph having a common item set including two or more kinds of items is a common subgraph CSG. For example, as the subgraph $\{v_1, v_4\}$ has a common item set $\{i_1, i_2\}$ (see FIG. 3), the subgraph $\{v_1, v_4\}$ is a common subgraph CSG. However, as addition of the vertex $v_3$ (see FIG. 2 and FIG. 4) adjacent to the vertex $v_4$, to the subgraph $\{v_1, v_4\}$ does not change the common item set, which rather remains unchanged as $\{i_1, i_2\}$, the subgraph $\{v_1, v_4\}$ is not a closed common subgraph CCSG. Meanwhile, the subgraph $\{v_1, v_3, v_4\}$, obtained by adding the vertex $v_3$ to the subgraph $\{v_1, v_4\}$, is a common subgraph CSG as having the common item set $\{i_1, i_2\}$ (see FIG. 3), and also a closed common subgraph CCSG as addition of any of the vertex $v_2, v_5, v_6$ adjacent to any of the vertexes $v_1, v_3, v_4$, to the subgraph $\{v_1, v_3, v_4\}$ changes the common item set from $\{i_1, i_2\}$ to $\{i_1\}$.

When the common item set of a closed common subgraph CCSG is the same as that of a common subgraph CSG that is not closed, the number of vertexes is larger with the former. For example, while the common item set of the subgraph $\{v_1, v_4\}$ and that of the subgraph $\{v_1, v_3, v_4\}$ are both $\{i_1, i_2\}$, the number of vertexes in the subgraph $\{v_1, v_3, v_4\}$, which is a closed common subgraph CCSG, is larger than that in the subgraph $\{v_1, v_4\}$, which is not a closed common subgraph CCSG.

Here, if it is possible to detect a common subgraph CSG that includes a larger number of vertexes, it will be possible to detect a larger number of genes as, e.g., genes having a direct or indirect relationship to one another whose expressions are changed in response to administration of a common drug, and accordingly, to identify a drug having influence on a larger number of genes. This is useful in, e.g., drug discovery. Further, for example, as it will become possible to detect a larger number of proteins as, e.g., proteins having a direct or indirect relationship to one another whose expressions are changed in response to administration of a common drug, it will be possible to identify a drug having influence on a larger number of proteins. This is useful in, e.g., drug discovery. Still further, for example, as it will become possible to detect a larger number of users as, e.g., users having direct or indirect friendship to one another and having purchased a common product, it will be possible to make an efficient product advertisement. In view of the above, a closed common subgraph CCSG, in particular, is detected in this embodiment in order to obtain a common subgraph CSG including a larger number of vertexes. Details of an operation of the subgraph detection unit 24 will be described later.

[5. Process]

A process carried out in the subgraph detection device 2 to detect a common subgraph CSG (a closed common subgraph CCSG in particular) will be described. In the following, a case in which the above described N is 2, that is, a case of detecting a common subgraph CSG in which the product set of the item sets I(v) correlated to the respective vertexes v includes two or more kinds of items i will be described.

[5-1. Outline of Process]

Figure 7:
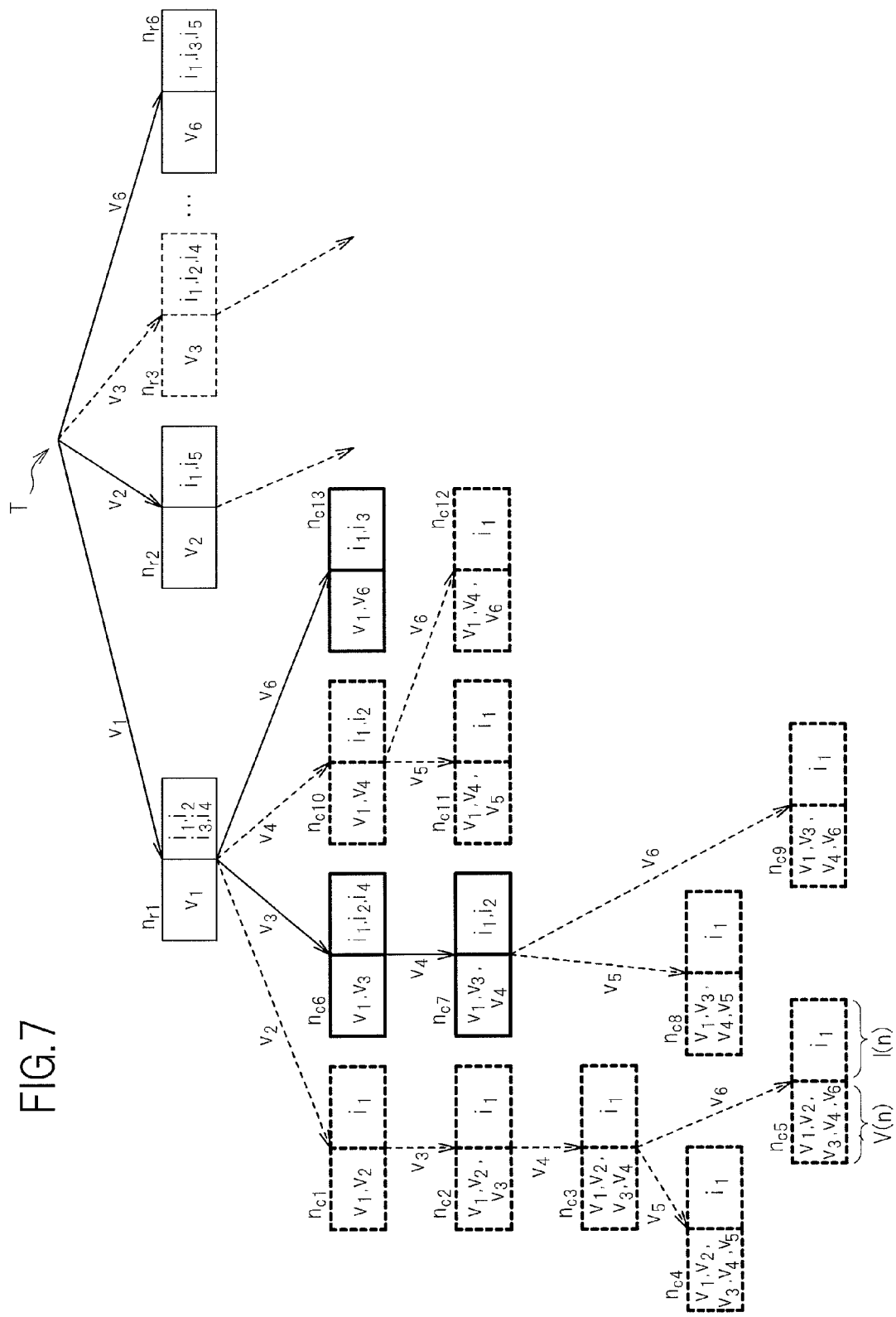
FIG. 7 is a diagram showing one example of a tree.

Initially, the process will be outlined. FIG. 7 is a diagram explaining an outline of the process. In the subgraph detection device 2, a tree T (a search tree), such as is shown in FIG. 7, is produced using a depth-first search algorithm in detection of a common subgraph CSG (a closed common subgraph CCSG, in particular). The tree T shown in FIG. 7 includes root nodes $n_r$ ($n_{r1}$ to $n_{r6}$) corresponding to the respective vertexes $v_1$ to $V_6$ of the graph G, and nodes $n_c$ ($n_{c1}$ to $n_{cM}$) subordinate to the root nodes $n_{r1}$ to $n_{r6}$. Each of the nodes n of the tree T shown includes a vertex set V(n) and a common item set I(n), in which a vertex set V(n) is a set of vertexes v included in the path led to that node n, and a common item set I(n) is a set of items i commonly possessed by all vertexes v included in the vertex set V(n). Specifically, in FIG. 7, a vertex set V(n) is shown on the left side of each node N, while a common item set I(n) is shown on the right side of the same. Note that, in the following, a vertex set V(n) included in a node n of the tree T will be referred to as a vertex set V(n) of a node n of the tree T, while an item set I(n) included in a node n of the tree T will be referred to as an item set I(n) of a node n of the tree T.

In the tree T shown in the diagram, a vertex set obtained by adding another vertex v to a vertex set $V(n_x)$ of each node (determined as a node $n_x$) constitutes a vertex set $V(n_{x+1})$ of a node $n_{x+1}$, or a child node of the node $n_x$. Specifically, a vertex set obtained by adding, as a new end vertex, one vertex adjacent to an end vertex in the vertex set $V(n_x)$ of a node $n_x$ to the vertex set $V(n_x)$ constitutes the vertex set $(n_{x+1})$ of a node $n_{x+1}$.

For example, a vertex set $\{v_1, v_2\}$ obtained by adding the vertex $v_2$ adjacent to an end vertex, or the vertex $\{v_1\}$, of the vertex set V ($n_{r1}$) of the node $n_{r1}$, to the vertex set $\{v_1\}$, constitutes the vertex set $V(n_{c1})$ of a node $n_{c1}$, or a child node of the node $n_{r1}$. In this case, the added vertex $v_2$ becomes an end vertex in the vertex set $V(n_{c1})$. Further, for example, a vertex set $\{v_1, v_2, v_3\}$ obtained by adding the vertex $v_3$ adjacent to an end vertex, or the vertex $\{v_2\}$, of the vertex set $V(n_{c1})$ of the node $n_{c1}$, to the vertex set $\{v_1, v_2\}$, constitutes the vertex set $V(n_{c2})$ of a node $n_{c2}$, or a child of the node $n_{c1}$. In this case, the added vertex $v_3$ becomes an end vertex in the vertex set $V(n_{c2})$. As described above, a vertex set obtained by adding a vertex adjacent to an end vertex in the vertex set $V(n_x)$ of a parent node $n_x$ to the vertex set $V(n_x)$ constitutes the vertex set $V(n_{x+1})$ of a child node $n_{x+1}$.

Each of the vertexes included in the vertex set V(n) of each node n is adjacent to any other vertex included in the vertex set V(n), and the vertex set V(n) of each node n constitutes a subgraph including the vertex set V(n).

The subgraph detection unit 24 makes each of the nodes n of the tree T a determination target in a search order according to a depth-first search algorithm. In the above, when the vertex set V(n) of a determination target node n includes a plurality of vertexes v, the subgraph detection unit 24 determines whether or not the subgraph constituted by the vertex set V(n) is a common subgraph CSG. That is, whether or not the product set of the item sets I(v) correlated to the respective vertexes v in the vertex set V(n) has two or more kinds of items is determined. In this manner, the subgraph detection unit 24 detects a common subgraph CSG, based on the tree T.

Note that although a depth-first search algorithm is employed here to produce the tree T, such as is shown in FIG. 7, a width-first search algorithm may be employed instead.

[5-2. Reference Set Table]

In the subgraph detection device 2, a reference set table is stored as data for avoiding an unnecessary process. In the following, a reference set table will be described.

Initially, the significance of providing a reference set table will be described. That is, when the below mentioned three relationships all hold between a node (determined as a "node $n_x$") and another node (determined as a "node $n_y$"), a subgraph including the vertex set $V(n_{xd})$ of a descendant node (determined as a "node $n_{xd}$") of the node $n_x$ is not a closed subgraph.

(Relationship 1)

An end vertex in the vertex set $V(n_x)$ of the node $n_x$ is the same as an end vertex in the vertex set $V(n_y)$ of the node $n_y$;

(Relationship 2)

The node $n_y$ is made a determination target before the node $n_x$; and (Relationship 3)

The common item set $I(n_y)$ of the node $n_y \supseteq$ the common item set $I(n_x)$ of the node $n_x$.

That a subgraph including the vertex set $V(n_{xd})$ of a node $n_{xd}$ is not a closed subgraph means that a subgraph including the vertex set $V(n_{xd})$ of the node $n_{xd}$ cannot be a closed common subgraph CCSG. Therefore, in this embodiment, when the above described relationships 1 to 3 all hold between a node $n_x$ (a first node) and another node $n_y$ (a second node), the subgraph detection unit 24 does not carry out determination with respect to the vertex set $V(n_{xd})$ of a descendant node $n_{xd}$ of the node $n_x$ as a determination target to see whether or not the subgraph constituted by the vertex set $V(n_{xd})$ is a common subgraph CSG. As a result, a closed common subgraph CCSG can be determined without carrying out determination with respect to all nodes n of the tree T as determination targets to see whether or not a subgraph constituted by the vertex set V(n) of a determination target node n is a common subgraph. This can reduce a processing load.

In the following, the reason why a subgraph constituted by the vertex set $V(n_{xd})$ of a descendant node $n_{xd}$ of a node $n_x$ cannot be a closed subgraph when the relationships 1 to 3 all hold between the node $n_x$ and another node $n_y$ will be described.

That is, when the node $n_y$ is a node produced before the node $n_x$ (relationship 2), and an end vertex in the vertex set $V(n_x)$ of the node $n_x$ is the same as an end vertex in the vertex set $V(n_y)$ of the node $n_y$ (relationship 1), the relationship "the vertex set $V(n_y)$ of the node $n_y \supseteq$ the vertex set $V(n_x)$ of the node $n_x$" (hereinafter referred to as "relationship 4") holds. For example, in FIG. 7, the relationship "the vertex set $V(n_{c7})$ of the node $n_{c7} \supseteq$ the vertex set $V(n_{c10})$ of the node $n_{c10}$" holds between the node $n_{c10}$ and the node $n_{c7}$ produced before the node $n_{c10}$.

Therefore, when a vertex set obtained by adding a vertex v adjacent to an end vertex in the vertex set $V(n_x)$ of the node $n_x$ to the vertex set $V(n_x)$ is the vertex set $V(n_{xd})$ of a descendant node $n_{xd}$ of the node $n_x$ and a vertex set obtained by adding the same vertex v to the vertex set $V(n_y)$ of the node $n_y$ is the vertex set $V(n_{yd})$ of a descendant node $n_{yd}$ of the node $n_y$, the relationship "the vertex set $V(n_{yd})$ of the node $n_{yd} \supseteq$ the vertex set $V(n_{xd})$ of the node $n_{xd}$" (hereinafter referred to as "relationship 5") holds between the vertex set $V(n_{xd})$ of the node $n_{xd}$ and the vertex set $V(n_{yd})$ of the node $n_{yd}$. For example, in FIG. 7, the relationship "the vertex set $V(n_{c8})$ of the node $n_{c8} \supseteq$ the vertex set $V(n_{c11})$ of the node $n_{c11}$" holds between the descendant node $n_{c8}$ of the node $n_{c7}$ and the descendant node $n_{c11}$ of the node $n_{c10}$.

In the above, when the relationship 5 holds, the number of items included in the product set (that is, the common item set $I(n_{yd})$) of the item sets correlated to the respective vertexes in the vertex set $V(n_{yd})$ of the node $n_{yd}$ is not larger than that of the items included in the product set (that is, the common item set $I(n_{xd})$) of the item sets correlated to the vertexes in the vertex set $V(n_{xd})$ of the node $n_{xd}$. This is because a larger number of vertexes included in a vertex set leads to a fewer number of items included in the product set of the item sets correlated to the respective vertexes in the vertex set. Therefore, when the relationship 5 holds, the relationship "the common item set $I(n_{yd})$ of the node $n_{yd} \subseteq$ the common item set $I(n_{xd})$ of the node $n_{xd}$" (hereinafter referred to as "relationship 6") holds.

Meanwhile, when "he common item set $I(n_y)$ of the node $n_y \supseteq$ the common item set $I(n_x)$ of the node $n_x$" (relationship 3) holds, the relationship "the common item set $I(n_{yd})$ of the node $n_{yd} \supseteq$ the common item set $I(n_{xd})$ of the node $n_{xd}$" (hereinafter referred to as "relationship 7") holds between the common item set $I(n_{xd})$ of the node $n_{xd}$ and the common item set $I(n_{yd})$ of the node $n_{yd}$ as the vertex set $V(n_{xd})$ of the node $n_{xd}$ and the vertex set $V(n_{yd})$ of the node $n_{yd}$ are vertex sets obtained by adding the same vertex v to the vertex set $V(n_x)$ and the vertex set $V(n_y)$, respectively.

As described above, when the above described relationships 1 to 3 all hold, the relationships 6, 7 also hold at the same time. A case in which the relationships 6, 7 hold at the same time refers to a case in which the common item set $I(n_{xd})$ of the node $n_{xd}$ and the common item set $I(n_{yd})$ of the node $n_{yd}$ hold the relationship "the common item set $I(n_{yd})$ of the node $n_{yd}$=the common item set $I(n_{xd})$ of the node $n_{xd}$". Therefore, when the relationships 1 to 3 all hold, the relationship "the item set $I(n_{yd})$ of the node $n_{yd}$=the item set $I(n_{xd})$ of the node $n_{xd}$" holds between the common item set $I(n_{yd})$ of the node $n_{yd}$ and the common item set $I(n_{xd})$ of the node $n_{xd}$. This means that addition of a vertex v included in the vertex set $V(n_{yd})$ of the node $n_{yd}$ but not in the vertex set $V(n_{xd})$ of the node $n_{xd}$ to the vertex set $V(n_{xd})$ of the node $n_{xd}$ does not change the common item set. That is, when the relationships 1 to 3 all hold between a node $n_x$ and another node $n_y$, the subgraph constituted by the vertex set $V(n_{xd})$ of a descendant node $n_{xd}$ of the node $n_x$ cannot be a closed subgraph.

For example, in the case shown in FIG. 7, the common item set $I(n_{c11})$ of a child node $n_{c11}$ of the node $n_{c10}$ and the common item set $I(n_{c8})$ of a child node $n_{c8}$ of the node $n_{c7}$ are both $\{i_1\}$, being equal to each other. That is, addition of the vertex $v_3$ included in the vertex set $V(n_{c8})$ of the node $n_{c8}$ but not in the vertex set $V(n_{c11})$ of the node $n_{c11}$ to the vertex set $V(n_{c11})$ of (the node $n_{c11}$ does not change the common item set, which remains as $\{i_1\}$. Therefore, the subgraph constituted by the vertex set $V(n_{c11})$ cannot be a closed subgraph.

Note that when the relationships 1 and 2 both hold, the relationship 4 holds, as described above. Therefore, that "when the relationships 1, 3, 4 all hold between a node $n_x$ and another node $n_y$, the above described determination is not carried out with respect to a child node $n_{cx}$ of the node $n_x$ (in other words, the vertex set $V(n_{xd})$ of the node $n_{cx}$) as a determination target" can be rephrased as that "when the relationships 1, 3, 4 all hold between a node $n_x$ and a node $n_y$, the above described determination is not carried out with respect to the vertex set $V(n_{xd})$ as a determination target".

Note that also when the respective nodes of the tree T are made a determination target in a search order according to a width-first search algorithm, it can be arranged such that determination as to whether or not a subgraph constituted by the vertex set $V(n_{xd})$ of a descendant node $n_{xd}$ of a node $n_x$ is a common subgraph CSG is not carried out when the above described relationships 1 and 3 and the relationship 2' described below all hold between the node $n_x$ (a first node) and another node $n_y$ (a second node).

(Relationship 2'): A node $n_x$ is made a determination target before a node $n_y$.

In the above described manner, also when the respective nodes of the tree T are made a determination target in a search order according to a width-first search algorithm, it is possible to detect a closed common subgraph CCSG without carrying out a determination with respect to all vertex sets V(n) as determination targets to see whether or not a subgraph constituted by the vertex set V(n) is a common subgraph CSG. This is because when the node $n_x$ is made a determination target before the node $n_y$ (Relationship 2'), the above described relationship 4 "the vertex set $V(n_y)$ of the node $n_y \supseteq$ the vertex set $V(n_x)$ of the node $n_x$" holds, with a search order according to a width first search algorithm taken into consideration, as long as an end vertex in the vertex set $V(n_x)$ of the node $n_x$ is the same as an end vertex in the vertex set $V(n_y)$ of the node $n_y$ (Relationship 1); therefore, since the above described relationships 1, 3, and 4 all hold, the above described relationships 5 to 7 also hold, similar to a case of the depth-first search algorithm employed; as a result, the relationship "the item set $I(n_{yd})$ of the node $n_{yd}$=the item set $I(n_{xd})$ of the node $n_{xd}$" holds; and therefore, addition of a vertex v included in the vertex set $V(n_{yd})$ of the node $n_{yd}$ but not in the vertex set $V(n_{xd})$ of the node $n_{xd}$ to the vertex set $V(n_{xd})$ of the node $n_{xd}$ does not change the common item set. In this case as well, it can be understood that when the above described relationships 1, 3, 4 all hold, the above described determination is not carried out with respect to a vertex set $V(n_{xd})$ as a determination target.

The reference set table is used in order to avoid, when the above described relationships 1 to 3 all hold between a node $n_x$ and anode $n_y$, the above described determination carried out with respect to the vertex set $V(n_{xd})$ of a child node $n_{cx}$ of the node $n_x$ as a determination target. FIG. 8 is a diagram showing one example of the reference set table. The reference set table is a table that correlates each of the vertexes v included in the graph G to reference sets P(v) including at least one reference set (that is, an item set I(n)) that is the product set of the item sets correlated to the respective vertexes in the vertex set V(n) including the vertex v as an end vertex. A role of the reference set table will be described later.

[5-3. Process Details]

Figure 9:
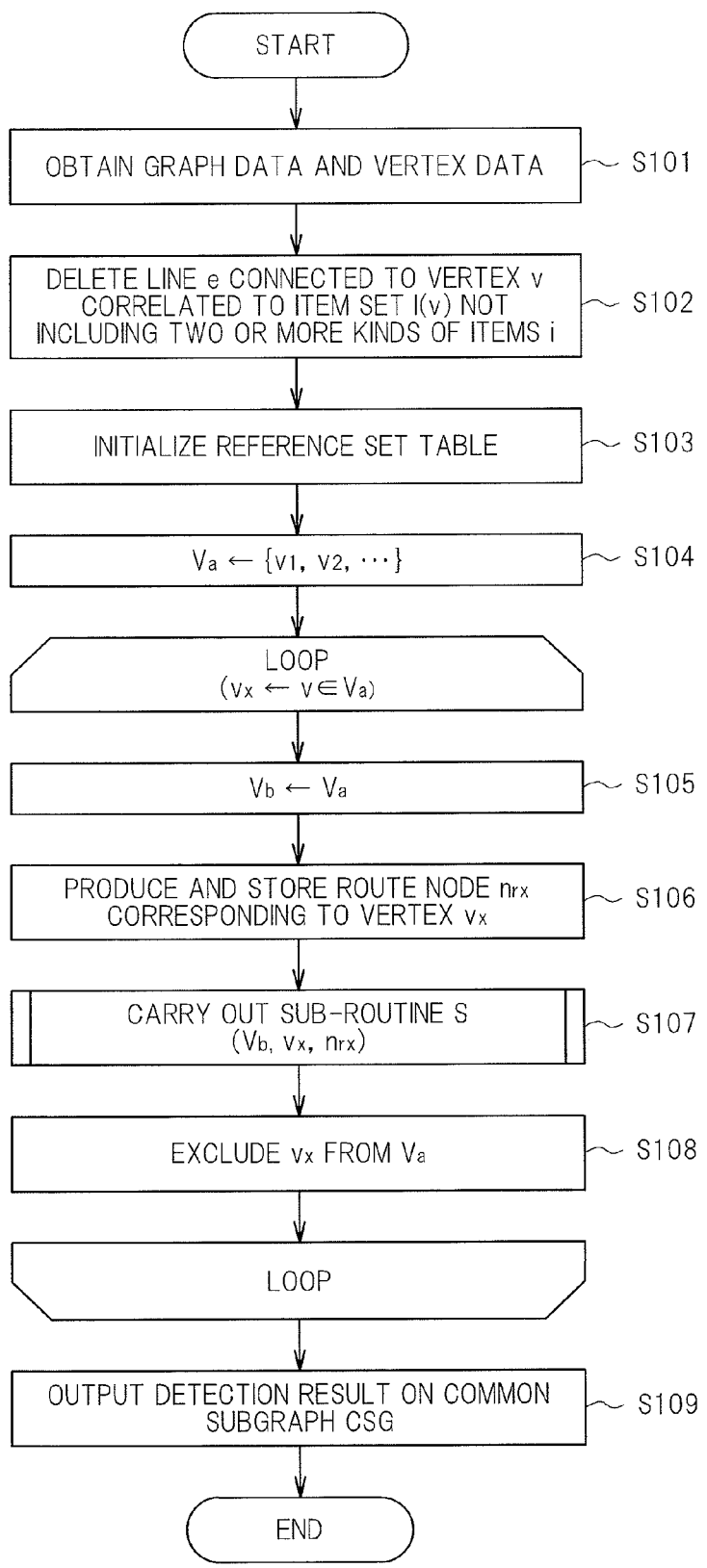
FIG. 9 is a flowchart of one example of a process carried out in a subgraph detection device according to an embodiment of the present invention.

FIG. 9 is a flowchart of a process carried out by the control unit 8. In the following, details of a process carried out by the control unit 8 will be described with reference to FIG. 9. Note that execution of the process shown in FIG. 9 by the control unit 8 realizes the graph data obtaining unit 20, the vertex data obtaining unit 22, and the subgraph detection unit 24. Note that the process at S101 in FIG. 9 corresponds to the graph data obtaining unit 20 and the vertex data obtaining unit 22, and the process at S102 and thereafter in FIG. 9 corresponds to the subgraph detection unit 24.

Initially, the control unit 8 carries out a pre-process (S101 to S104) for detecting a common subgraph CSG.

That is, initially, the control unit 8 reads and thereby obtains graph data and vertex data from the database 4 (S101), and then processes the graph data read. Specifically, a link e connected to a vertex v correlated to an item set I(v) that does not include two or more kinds of items i is deleted to thereby disconnect a relationship to other vertexes v (S102). Here, note that as a common subgraph CSG is determined to be a subgraph including vertexes v all having two or more kinds of common items, as described above, a vertex v correlated to an item set I(v) that does not include two or more kinds of items i, that is, a subgraph including a vertex v that does not include two or more kinds of items i, cannot be a common subgraph CSG. In view of the above, the process at S102 is carried out in order to ignore such a vertex v in the process at S103 and thereafter. With the process at S102 carried out, a redundant process is not carried out, so that a time period necessary to detect a common subgraph CSG can be reduced.

Thereafter, the control unit 8 initializes the reference set table (S103). Specifically, the reference sets P(v) of the respective vertexes v are initialized to be null. In addition, the control unit 8 obtains a set of vertexes v included in the graph G as a vertex set $V_a$ (S104).

Then, while sequentially selecting the respective vertexes v included in the vertex set $V_a$ as a process target vertex $v_x$, the control unit 8 carries out the process at S105 to S108. For example, with the vertex $v_1$ selected, the process at S105 to S108 is carried out, whereby a node $n_c$ subordinate to the root node $n_{r1}$ corresponding to the vertex $v_1$ in the tree T shown in FIG. 7 is produced, and detection of a common subgraph CSG including the vertex $v_1$ is carried out.

Initially, the control unit 8 obtains a set of the vertexes v included in the vertex set $V_a$ as a vertex set $V_b$ (S105). Thereafter, the control unit 8 produces a root node n, corresponding to a vertex $v_x$, and stores in the storage unit 10 (S106). For example, for the vertex $v_x$ being the vertex $v_1$, a root node $n_{r1}$ is produced in which the vertex set $V(n_{r1})$ of the root node $n_{r1}$ is $\{v_1\}$ and the common item set $I(n_{r1})$ is $\{i_1, i_2, i_3, i_4\}$. Note that an end vertex in the vertex set $V(n_{r1})$ is $v_1$. Thereafter, the control unit 8 carries out a sub-routine S (S107).

Figure 10:
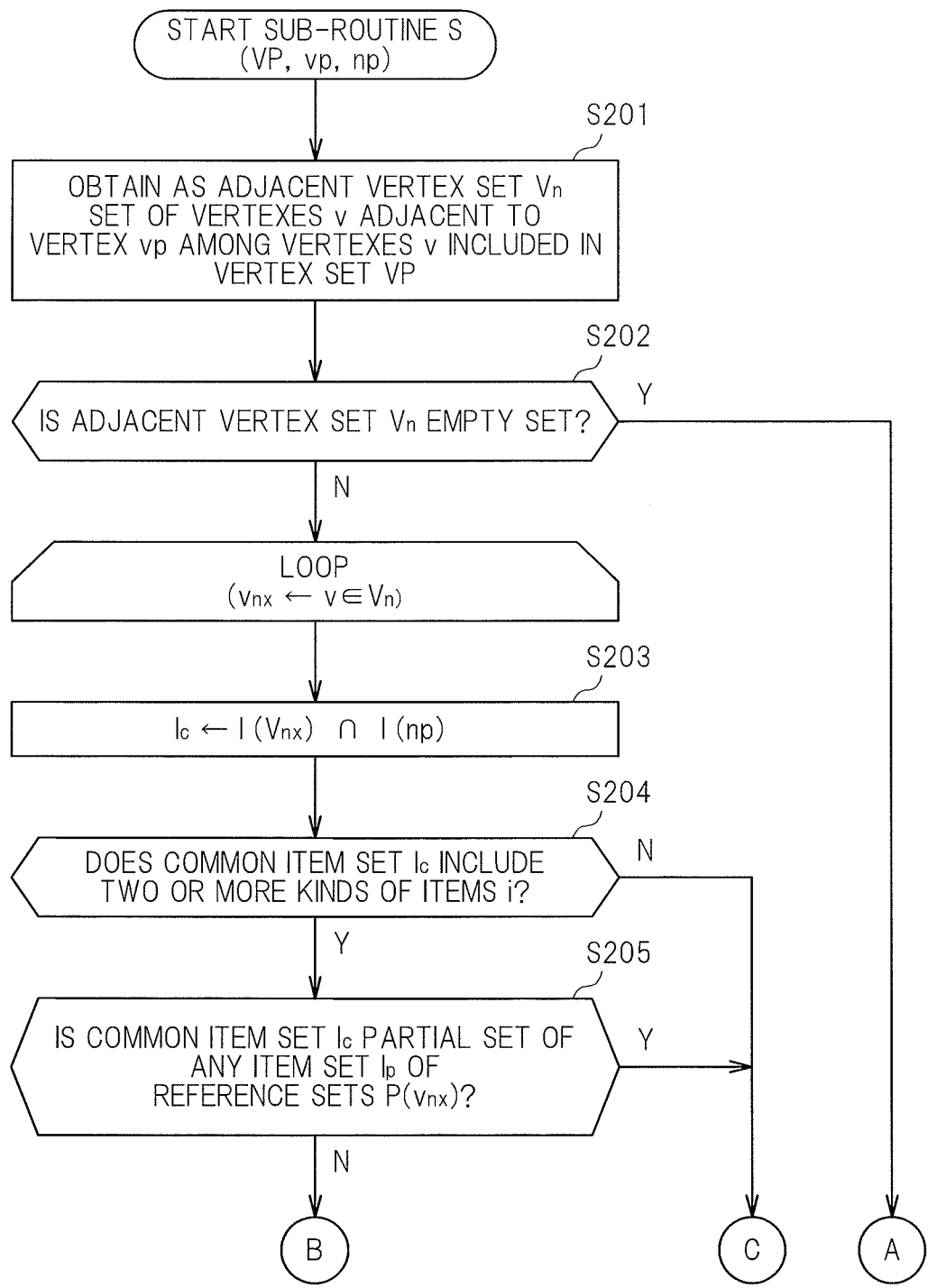
FIG. 10 is a flowchart of one example of a process carried out in a subgraph detection device according to an embodiment of the present invention.
Figure 11:
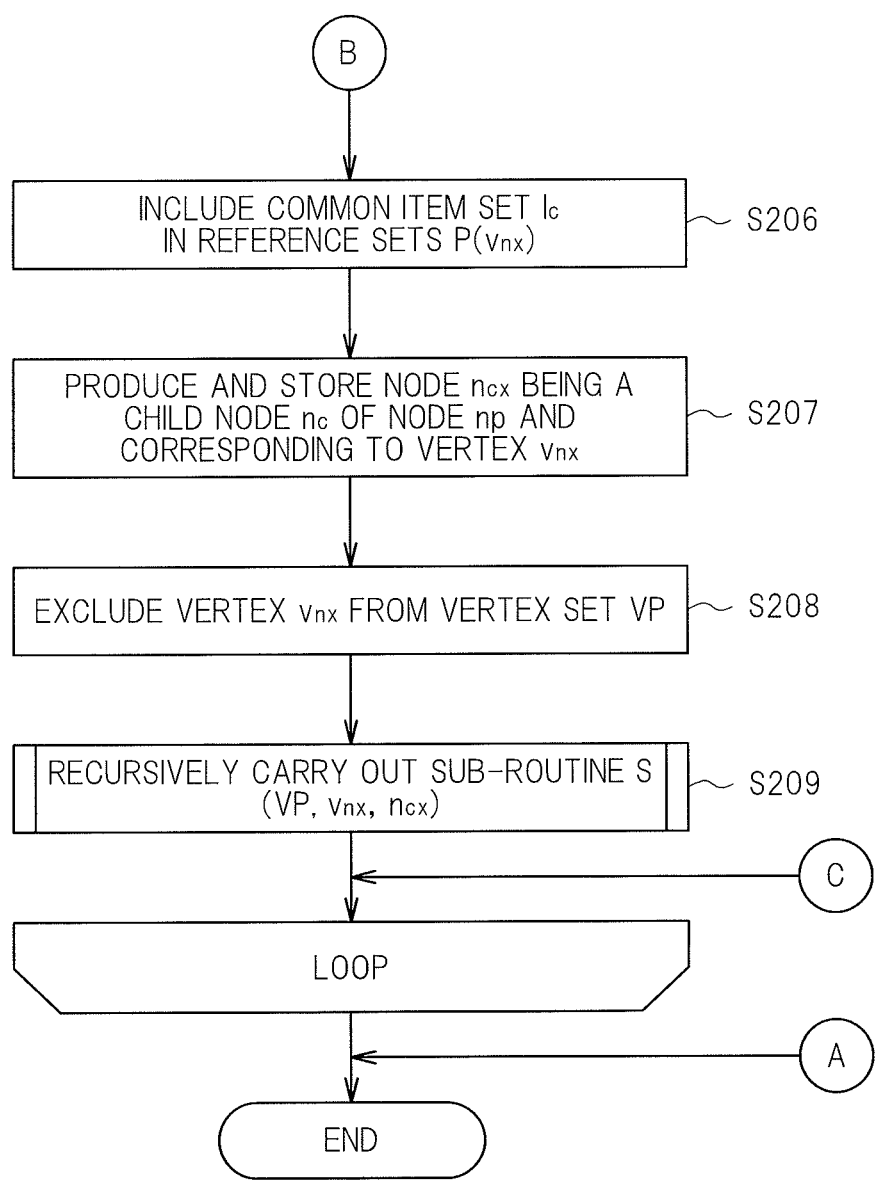
FIG. 11 is a flowchart of one example of a process carried out in a subgraph detection device according to an embodiment of the present invention.

In the following, the sub-routine S will be described. FIGS. 10 and 11 show a flowchart of a process of the sub-routine S. The sub-routine S has three arguments, namely, an argument VP corresponding to a vertex set, an argument vp corresponding to one vertex v, and an argument np corresponding to one node n of the tree T. In the process at S107, the sub-routine S is called up with the vertex set $V_b$ as the argument VP, the vertex $v_x$ as the argument vp, and the root node $n_{rx}$ as the argument np.

As shown in FIG. 10, in the sub-routine S, initially, a set of the vertexes v adjacent to a vertex vp among the vertexes v included in the vertex set VP is obtained as an adjacent vertex set $V_n$ (S201). Then, the control unit 8 determines whether or not the adjacent vertex set $V_n$ is an empty set (S202). When the adjacent vertex set $V_n$ is an empty set (Y at S202), that is, when there is no vertex v adjacent to the vertex vp among the vertexes v included in the vertex set VP, the control unit 8 terminates the sub-routine S, and carries out the process at S108 in FIG. 9 instead. That is, the vertex $v_x$ is excluded from the vertex set $V_a$ (S108), and another vertex v is selected from the vertex set $V_a$ as a new process target vertex $v_x$ before the process at S105 to S108 is carried out.

Meanwhile, when the adjacent vertex set $V_n$ is not an empty set (N at S202), the control unit 8 sequentially selects the respective vertexes v included in the adjacent vertex set $V_n$ as a process target vertex $v_{nx}$ and carries out the process at S203 to S209.

Initially, with reference to the vertex data, the control unit 8 obtains the item set $I(v_{nx})$ correlated to the vertex $v_{nx}$, and then obtains as a common item set $I_c$ the product set of the item set $I(v_{nx})$ and the common item set I(np) of the node np of the tree T (S203). Note that the common item set I(np) of the node np refers to the product set of the item sets I(v) correlated to the respective vertexes v in the vertex set V(np) of the node np, as described above.

Then, the control unit 8 (determination unit) determines whether or not the common item set $I_c$ includes two or more kinds of items i (S204). Note that in the process at S204, the determination is carried out with respect to a subgraph constituted by a vertex set obtained by adding a vertex $v_{nx}$ to the vertex set V(np) of the node np as a determination target to see whether or not all vertexes v in the subgraph have two or more kinds of common items. That is, whether or not a subgraph obtained by adding the vertex $v_{nx}$ to the vertex set V(np) of the node np is a common subgraph CSG is determined.

Note that a vertex set obtained by adding a vertex $v_{nx}$ adjacent to the vertex vp (an end vertex) in the vertex set V(np) of a node np to the vertex set V(np) corresponds to a child node of the node np. Further, the common item set $I_c$ obtained at S203 corresponds to the common item set of all vertexes v in the vertex set (a subgraph) of a child node of the node np. Therefore, it can be rephrased that whether or not all vertexes v in the vertex set (a subgraph) of a child node of the node np have two or more kinds of common items is determined in the process at S204. That is, this can be further rephrased that whether or not a vertex set (a subgraph) of a child node of the node np is a common subgraph CSG is determined.

When the common item set $I_c$ includes two or more kinds of items (Y at S204), the control unit 8 reads the reference sets P($v_{nx}$) corresponding to the vertex $v_{nx}$ from the reference set table (see FIG. 8), and determines whether or not the common item set $I_c$ is a subset of any reference set $I_p$ included in the reference sets P($v_{nx}$) (S205). A role of this process will be described later.

When the common item set $I_c$ is not a subset of any reference set $I_p$ (N at S205), the control unit 8 includes the common item set $I_c$ as a reference set $I_p$ in the reference sets P($v_{nx}$) corresponding to the vertex $v_{nx}$ in the reference set table (see FIG. 8) stored in the storage unit 10 (reference set storage means) (S206). Thereafter, the control unit 8 produces a child node $n_{cx}$ being a child node $n_c$ of the node np in the tree T and corresponding to the vertex $v_{nx}$, and stores in the storage unit 10 (S207). In this case, the vertex set V($n_{cx}$) of the node $n_{cx}$ is set to a vertex set obtained by adding the vertex $v_{nx}$ to the vertex set V(np) of the node np, and the common item set I($n_{cx}$) is set to the common item set $I_c$. An end vertex in the vertex set V($n_{cx}$) is the vertex $v_{nx}$.

Note that the node $n_{cx}$ produced at S207 shows one common subgraph CSG. This is because the vertex set V($n_{cx}$) of the node $n_{cx}$ is a set of vertexes v, and the common item set I($n_{cx}$) refers to a set of items i commonly possessed by the vertexes v included in the vertex set V($n_{cx}$) and includes two or more kinds of items (see S204). Therefore, production of a node $n_{cx}$ corresponds to detection of a common subgraph CSG.

Thereafter, the vertex $v_{nx}$ is excluded from the vertex set VP (S208), and the sub-routine S is recursively called up (S209). In this case, the sub-routine S is called up with the vertex set VP as the argument VP, the vertex $v_{nx}$ as the argument vp, and the node $n_{cx}$ produced at S207 as the argument np. With the sub-routine S called up, a node $n_c$ subordinate to the node $n_{cx}$ in the tree T shown in FIG. 7 is produced.

Note that when it is determined in the process at S204 that the common item set $I_c$ does not include two or more kinds of items (N at S204), the control unit 8 (control means) does not carry out the process at S205 to S209. In this case, another vertex v included in the adjacent vertex set $V_n$ is selected as a new process target vertex $v_{nx}$, and the process at S203 is carried out.

In the following, a role of the process at S204 will be described based on an assumption here that the sub-routine S is called up in the process at S107 with the node $n_{r1}$ as the argument np, and that the vertex $v_2$ is selected as a process target vertex $v_{nx}$ in the process at S204. In this case, as described above, whether or not the vertex set $\{v_1, v_2\}$ obtained by adding the vertex $v_2$ to $\{v_1\}$, or the vertex set V($n_{r1}$) of the node $n_{r1}$, in other words, the vertex set $\{v_1, v_2\}$ corresponding to the child node $n_{c1}$ of the node $n_{r1}$, is a common subgraph CSG is determined. That is, whether or not the subgraph $\{v_1, v_2\}$ is a common subgraph CSG is determined. As an item i commonly possessed by the vertex $v_1$ and the vertex $v_2$ is only the item $i_i$ (see FIG. 3), it is determined in the process at S204 that the common item set $I_c$ does not include two or more kinds of items i. That is, it is determined that the subgraph $\{v_1, v_2\}$ is not a common subgraph CSG. As a result, the process at S205 to S209 is not carried out, and accordingly, the node $n_{c1}$ shown in FIG. 7 is not produced. Further, the sub-routine S with the vertex $v_{nx}$ ($v_2$) as the argument vp and the node $n_{c1}$ as the argument np is not called up, and accordingly the nodes $n_{c2}$ to $n_{c5}$ subordinate to the node $n_{c1}$ shown in FIG. 7 are not produced. That is, determination as to whether or not the subgraph constituted by the vertex set V(nx) is a common subgraph CSG is not carried out with respect to the vertex set V(nx) of a descendant node (determined as a "node nx") of the node $n_{c1}$ as a determination target.

For example, when the sub-routine S with the vertex $v_{nx}$ ($v_2$) as the argument vp and the node $n_{c1}$ as the argument np is called up, whether or not the vertex set $\{v_1, v_2, v_3\}$, or the subgraph $\{v_1, v_2, v_3\}$, obtained by adding a vertex $v_3$ adjacent to the vertex $v_{nx}$ ($v_2$), to $\{v_1, v_2\}$, or the vertex set V($n_{c1}$) of the node $n_{c1}$, is a common subgraph CSG is determined in the process at S204. For example, when the respective vertexes v in the subgraph $\{v_1, v_2\}$ do not possess two or more kinds of common items i and accordingly the subgraph $\{v_1, v_2\}$ is not a common subgraph CSG, naturally, the subgraph $\{v_1, v_2, v_3\}$ obtained by adding the vertex $v_3$ to the subgraph $\{v_1, v_2\}$ cannot be a common subgraph CSG. Therefore, the above described determination process is unnecessary. Regarding this point, in this embodiment, when it is determined in the process at S204 that the subgraph $\{v_1, v_2\}$ is not a common subgraph CSG, the process at S205 to S209 is not carried out, and accordingly, determination as to whether or not the subgraph $\{v_1, v_2, v_3\}$ is a common subgraph CSG is not carried out. That is, an unnecessary process is not carried out.

Further, when it is determined in the process at S205 that the common item set $I_c$ is a subset of any reference set $I_p$ included in the reference sets P($v_{nx}$), the control unit 8 (control means) does not carry out the process at S206 and thereafter. In this case, another vertex n included in the adjacent vertex set $V_n$ is selected as a new vertex $v_{nx}$, and the process at S203 is carried out.

In the following, roles of the reference set table (see FIG. 8) and the process at S205 will be described based on an assumption that, e.g., the sub-routine S shown in FIG. 11 is called up in the process at S209 in FIG. 11 with the vertex $v_3$ as the argument vp and the node $n_{c6}$ as the argument np, and that the process at S203 to S206 is carried out with the vertex $v_4$ as a process target vertex $v_{nx}$. In this case, as described above, whether or not the vertex set $\{v_1, v_3, v_4\}$, obtained by adding a vertex $v_4$ adjacent to the vertex $v_{nx}$ ($v_3$), to $\{v_1, v_3\}$, or the vertex set V($n_{c6}$) of the node $n_{c6}$, in other words, the vertex set $\{v_1, v_3, v_4\}$ corresponding to the node $n_{c72}$, is a common subgraph CSG is determined in the process at S204. That is, whether or not the subgraph $\{v_1, v_3, v_4\}$ is a common subgraph CSG is determined. As an item i commonly possessed by the vertexes $v_1, v_3, v_4$ is the items $i_1, i_2$ (see FIG. 3), it is determined in the process at S204 that the common item set $I_c\{i_1, i_2\}$ includes two or more kinds of items i. That is, the subgraph $\{v_1, v_3, v_4\}$ is determined as a common subgraph CSG. Further, according to the reference set table at the time (see FIG. 8), the reference sets $P(v_4)$ corresponding to the vertex $v_4$ are null, or the initial state, it is determined in the process at S205 that the common item set $I_c\{i_1, i_2\}$ is not a subset of any reference set $I_p$ included in the reference sets $P(v_4)$. As a result, the process at S206 is carried out, and a common item set $I_c\{i_1, i_2\}$ is included as a reference set in the reference sets $P(v_4)$ corresponding to the vertex $v_4$ in the reference set table (see FIG. 8).

In the following, assume a case in which the sub-routine S is called up at S107 in FIG. 9 with the vertex $v_1$ as the argument vp and the node $n_{r1}$ as the argument np, and the process at S203 to S205 is carried out with the vertex $v_4$ as a process target vertex $v_{nx}$. In this case, as described above, whether or not the vertex set $\{v_1, v_4\}$ obtained by adding, as an end vertex, the vertex $v_4$ adjacent to the vertex $v_1$, to $\{v_1\}$, or the vertex set $V(n_{r1})$ of the node $n_{r1}$, in other words, the vertex set $\{v_1, v_4\}$ corresponding to the node $n_{c10}$, is a common subgraph CSG is determined in the process at S204. That is, whether or not the subgraph $\{v_1, v_4\}$ is a common subgraph CSG is determined. Then, as an item i commonly possessed by the vertexes $v_1, v_4$ is the items $i_1, i_2$ (see FIG. 3), it is determined in the process at S204 that the common item set $I_c\{i_1, i_2\}$ includes two or more kinds of items i, and accordingly the subgraph $\{v_1, v_4\}$ is determined as a common subgraph CSG. Here, according to the reference set table at the time (see FIG. 8), the reference set $I_p\{i_1, i_2\}$ is included in the reference sets $P(v_4)$ corresponding to the vertex $v_4$, in which the reference set $I_p\{i_1, i_2\}$ is the common item set $I(n_{c7})$ of the node $n_{c7}$ already produced. That is, as the reference set $I_p\{i_1, i_2\}$ is included in the reference sets $P(v_4)$ corresponding to the vertex $v_4$, it is determined in the process at S205 that the common item set $I_c\{i_1, i_2\}$ of the subgraph $\{v_1, v_4\}$ is a subset of any reference set $I_p$ included in the reference sets $P(v_4)$, and as a result, the process at S206 to S208 is not carried out. That is, the process at S207 is not carried out, and the node $n_{c10}$ shown in FIG. 7 is not produced. Further, the process at S208 is not carried out, and the sub-routine S with the vertex $v_{nx}$ ($v_4$) as the argument vp and the node $n_{c10}$ as the argument np is not called up. As a result, the node $n_{c11}$ to $n_{c12}$ subordinate to the node $n_{c10}$ shown in FIG. 7 are not produced. That is, the vertex set V(nx) of a descendant node (determined as a "node nx") of the node $n_{c10}$ is not obtained as a determination target, and accordingly determination as to whether or not a subgraph constituted by the vertex set V(nx) is a common subgraph CSG is not carried out.

When the sub-routine S with, e.g., the vertex $v_{nx}$ ($v_4$) as the argument vp and the node $n_{c10}$ as the argument np is called up, the vertex set $\{v_1, v_4, v_5\}$, or the subgraph $\{v_1, v_4, v_5\}$, obtained by adding a vertex $v_5$ adjacent to the vertex $v_{nx}$ ($v_4$), to $\{v_1, v_4\}$, or the vertex set $V(n_{c10})$ of the node $n_{c10}$, is a common subgraph CSG is determined in the process at S204. Regarding this point, in this embodiment, when it is determined in the process at S205 that the common item set $I_c\{i_1, i_2\}$ of the subgraph $\{v_1, v_4\}$ is a subset of any reference set $I_p$ included in the reference sets $P(v_4)$, the process at S205 to S209 is not carried out, and accordingly, determination as to whether or not the subgraph $\{v_1, v_4, v_5\}$ constituted by the vertex set $V(n_{c11})$ of the child node $n_{c11}$ of the node $n_{c10}$ is a common subgraph CSG is not carried out.

A case in which it is determined in the process at S205 that the common item set $I_c\{i_1, i_2\}$ of the subgraph $\{v_1, v_4\}$ is a subset of any reference set $I_p\{i_1, i_2\}$ included in the reference sets $P(v_4)$ refers to a case in which there is no possibility, as to a subgraph including the vertex $v_4$, of detection of a common item set that is not included in a common item set already detected.

Further, a case in which it is determined in the process at S205 that the common set $I_c\{i_1, i_2\}$ of the subgraph $\{v_1, v_4\}$ is a subset of any reference set $I_p\{i_1, i_2\}$ included in the reference sets $P(v_4)$ refers to a case in which the common item set $I(n_{c10})$ of the node $n_{c10}$ is included in the common item set $I(n_{c7})$ of the node $n_{c7}$ already produced as the reference set $I_p\{i_1, i_2\}$ corresponds to the common item set $I(n_{c7})$ of the node $n_{c7}$ already produced, as described above. Further, as an end vertex in the vertex set $V(n_{c7})$ of the node $n_{c7}$ and that of the vertex set $V(n_{c10})$ of the node $n_{c10}$ are both vertex $v_4$, a case in which it is determined in the process at S205 that the common item set $I_c\{i_1, i_2\}$ of the subgraph $\{v_1, v_4\}$ is a subset of any reference set $I_p\{i_1, i_2\}$ included in the reference sets $P(v_4)$ refers to a case in which, supposing that the node $n_{c7}$ is the node $n_y$ and the node $n_{c10}$ is the node $n_x$, the above described relationships 1 to 3 all hold between the node $n_y$ and the node $n_x$. In such a case, as it is obvious that the vertex set $\{v_1, v_4, v_5\}$, or the subgraph $\{v_1, v_4, v_5\}$, obtained by adding the vertex $v_5$ to the subgraph $\{v_1, v_4\}$ is not a closed subgraph, there is no need of carrying out a determination process to determine whether or not the subgraph $\{v_1, v_4, v_5\}$ is a common subgraph CSG. Regarding this point, such an unnecessary determination process is not carried out in this embodiment.

With the process at S105 to S108 carried out with respect to all vertexes v, as shown in FIG. 9, the control unit 8 outputs a result of the detection of a common subgraph CSG (S109). As described above, the node $n_c$ of the tree T stored in the storage unit 10 indicates a common subgraph CSG (a closed common subgraph CCSG in this embodiment). In the process at S109, a common subgraph CSG such as one having, e.g., the maximum number of vertexes v or links e is output to be displayed based on the node $n_c$ of the tree T stored in the storage unit 10. Alternatively, a common subgraph CSG such as one having, e.g., the number of vertexes v or links e larger than a predetermined reference number may be output to be displayed. Still alternatively, all detected common subgraphs CSG may be output to be displayed. The above described is details of the process carried out in the subgraph detection device 2.

[5. Conclusion]

In the above-described subgraph detection system 6, graph data of a graph G including, e.g., a plurality of vertexes $v_i$ corresponding to a plurality of genes and showing relationship among the plurality of genes is stored. In addition, vertex data that correlates an item set $I(v_1)$ to each of the plurality of vertexes $v_i$ is stored, in which the vertex data is data indicating a drug that changes expression of a respective gene. Based on the data, a common subgraph CSG showing genes having a direct or indirect relationship to one another whose expressions are commonly changed in response to administration of a common drug is detected in the subgraph detection device 2. Use of a result of the detection can provide useful information in, e.g., narrowing down genes to be a drug discovery target.

Further, for example, in the subgraph detection system 6, graph data of a graph G including, e.g., a plurality of vertexes $v_i$ corresponding to a plurality of proteins and showing relationship among the plurality of proteins is stored, and vertex data indicating a drug that changes expression of the respective proteins is stored. In this case, a common subgraph CSG showing proteins having a direct or indirect relationship to one another whose expressions are commonly changed in response to administration of a common drug is detected. Use of a result of the detection can provide useful information in, e.g., narrowing down proteins to be a drug discovery target.

Further, for example, in the subgraph detection system 6, graph data of a graph G including, e.g., a plurality of vertexes $v_i$ corresponding to a plurality of users and showing friendship among the plurality of users is stored, and vertex data indicating a product purchased by the respective user is stored. In this case, a common subgraph CSG showing users having direct or indirect friendship to one another and having purchased a common product is detected. Use of a result of the detection enables an efficient advertisement of a product, as described above.

It should be noted here that even when at least one of S204 and S205 in FIG. 10 is omitted, detection of a common subgraph CSG is possible. For example, even when at least one of S204 and S205 in FIG. 10 is omitted, detection of a closed common subgraph CCSG is possible. Here, for example, it is expected that the above described determination process is carried out with respect to all vertex sets, that is, all subgraphs, as determination targets to detect all common subgraphs and to specify a closed common subgraph among those common subgraphs. In this case, however, for example, when the number of vertexes v included in the graph G is enormous (e.g., 10000), a huge amount of time period may possibly be necessary to detect all common subgraphs CSG.

Regarding this point, in the above-described subgraph detection device 2, for example, execution of the process at S204 or S205 in FIG. 10 can prevent execution of an unnecessary process. That is, the above described determination process is not carried out with respect to a subgraph that is not a closed subgraph as a determination target. This can reduce a time period necessary to detect a common subgraph CSG (a closed common subgraph CCSG). Accordingly, detection of a common subgraph CSG (a closed common subgraph CCSG) can be completed in a relatively short time period even when the number of vertexes v included in the graph G is enormous.

[6. Modified Examples]

Note that the present invention is not limited to the above-described embodiment.

[6-1. First Modified Example]

For example, in the process shown in FIG. 9 to FIG. 11, when the above described relationships 1 to 3 all hold between a node $n_x$ having a vertex set $V(n_x)$ that includes a plurality of vertexes and another node $n_y$, the above described determination process with respect to the vertex set $V(n_{xd})$ of a node $n_{xd}$, or a descendant of the node $n_x$, as a determination target is omitted. Alternatively, the above described determination process with respect to the vertex set $V(n_{xd})$ of a node $n_{xd}$, or a descendant of the node $n_x$, as a determination target may be omitted when the above described relationships 1 to 3 (or the above described relationships 1, 3, 4) all hold between a node $n_x$ (a third node) having a vertex set $V(n_x)$ that includes only one vertex and a node $n_y$ (a fourth node).

For example, the control unit 8 may carry out a process similar to the process at S205 in FIG. 10 before carrying out the process at S107 in FIG. 9. That is, the control unit 8 may obtain the reference sets $P(v_x)$ corresponding to a vertex $v_x$ from the reference set table (see FIG. 8), and determine whether or not the item set $I(v_x)$ of the vertex $v_x$ is a subset of any item set $I_p$ included in the reference sets $P(v_x)$. When the item set $I(v_x)$ is not a subset of any item set $I_p$, the process at S107 may be carried out, and when the item set $I(v_x)$ is a subset of any item set $I_p$, the process at S108 may be carried out instead of the process at S107. In this manner as well, execution of an unnecessary process for detecting a common subgraph CSG (a closed common subgraph CCSG) can be refrained.

Further, in a case in which the respective nodes of the tree T are made a determination target in a search order according to a width-first search algorithm, when the above described relationships 1, 2', 3 (or the above described relationships 1, 3, 4) all hold between a node $n_x$ (a third node) having a vertex set $V(n_x)$ including only one vertex and a node $n_y$ (a fourth node), the above described determination process with respect to the vertex set $V(n_{xd})$ of a node $n_{xd}$, or a descendant of the node $n_x$, as a determination target may be omitted. With the above, execution of an unnecessary process for detecting a common subgraph CSG (a closed common subgraph CCSG) can be prevented also when the respective nodes of the tree T are made a determination target in a search order according to a width-first search algorithm.

[6-2. Second Modified Example]

A process for detecting a common subgraph CSG is not limited to the above described process. For example, a reference item set $I_d$ including an N or larger number of kinds of items i may initially be determined, and thereafter, a common subgraph CSG in which the item sets $I(v)$ correlated to the respective vertexes v include the reference item set $I_d$ may be determined. In this case, the control unit 8 may determine in the process at S203 in FIG. 10 whether or not the item set $I_d$ is a subset of the common item set $I_c$.

[6-3. Third Modified Example]

For example, the item i in the vertex data shown in FIG. 5 may correspond to a service which a user uses or used in the past. In this case, the vertex data is data indicating a service which each user uses or used in the past. In this manner, users having direct or indirect friendship to one another and using or having used a common service can be detected, and accordingly, use of a result of the detection enables, e.g., an efficient advertisement of a service.

[6-4. Fourth Modified Example]

For example, the graph data may be data of a graph including a plurality of vertexes v corresponding to a plurality of documents and showing relationship (e.g., reference relationship) among the plurality of documents. In the graph, for example, when a first document refers to a second document, the vertex $v_1$ corresponding to the first document is connected to the vertex $v_2$ corresponding to the second document via the link $e_{12}$. In this case, the item in the vertex data may correspond to, e.g., a key word correlated to a document. In this case, the vertex data is data indicating a key word of each document. According to the fourth modified example, documents having direct or indirect reference relationship to one another and a common key word set thereon can be detected based on the above-described graph data and vertex data. Note that, for example, the item i may correspond to a writer of a document.

[6-5. Others]

The graph G may be a graph indicating a relationship of anything other than a gene, a protein, a user, and a document. That is, a vertex v included in the graph G may be a vertex corresponding to anything other than a gene, a protein, a user, and a document. Information correlated to a vertex v in the vertex data may not be limited to information relating to a user, a key word, or a drug, and may be any information other than connection relationship information among the vertexes.

Although a graph G that is a non-directed graph has been described in the above, the graph G may be a directed graph. In this case, the tree T shown in FIG. 7 is produced in consideration of the digraph structure. For example, at S201 in FIG. 10, the control unit 8 may obtain as an adjacent vertex set V, a set of vertexes v connected to a link extending from a vertex vp among the vertexes v adjacent to the vertex vp included in the vertex set VP.

[7. Experiment]

An experiment was carried out using the method A according to the present invention and another method B to detect a set C of closed common subgraphs CCSG each including an M or larger number of links. Details and result of the experiment will be described below.

Assume here that a set C of closed common subgraphs CCSG satisfying all of the conditions described below were to detect:

two or more kinds of common items were included in any closed common subgraph CCSG in the set C (two or more kinds of items were included in the product set of the common item sets of the respective closed common subgraphs CCSG); and none of the closed common subgraphs CCSG included in the set C shared a vertex with any other closed common subgraph CCSG included in the set C.

The machine environment described below was prepared in the experiment:

CPU: 3.2 GB AMD Opteron (registered trademark)
memory capacity: 1 GB
OS: Linux (kernel 2.6)

(Method A)

Phase A1: carry out the process shown in FIGS. 9 to 11 to specify a closed common subgraph CCSG;

Phase A2: specify a closed common subgraph CCSG including an M or larger number of links from among the closed common subgraphs CCSG specified at the phase A1; and Phase A3: detect the set C based on the common item set of the closed common subgraphs CCSG specified at the phase A2.

(Method B)

Phase B1: detect a frequent item set including two or more kinds of items, using an Apriori method, in which a frequent item set referred to an item set that is included to an itemset an F or larger number of vertexes were collated to, and free data mining software "Weka" was used to detect a frequent item set in this experiment; and Phase B2: specify for every frequent item set a closed common subgraph CCSG including vertexes correlated to the item sets, including the frequent item set, and having an "M" or larger number of links, to thereby detect the set C.

Note that when the "F" was set to "2" and the "M" was set to "1" for the method B, a closed common subgraph CCSG that was the same as the closed common subgraph CCSG specified at the phase A1 of the method A was specified.

In the first experiment, the "F" was set to "2" and the "M" was set to "10", and the set C was then detected in the experimental target graph. Note that a graph in which a vertex corresponded to a "document", a link corresponded to "reference relationship among documents", and an item correlated to a vertex corresponded to "a writer of a document" was used as an experimental target graph. Note that the total number of writers was 16638. The numbers of vertexes and links in the experimental target graph were as follows:

the number of vertexes: 22178
the number of links: 112304

According to the method A, detection of the set C was completed in 7.9 seconds. Meanwhile, according to the method B, the memory ran short in 101 seconds after the experiment started, and as a result, the process was forcibly terminated. This was considered because a huge number of frequent item set candidates were produced for detection of a frequent item set at the phase B1.

In another experiment, the "F" was set to "4" and the "M" was set to "7", and the set C was then detected in the experimental target graph. Note that a graph in which a vertex corresponded to a "gene", a line corresponded to "an interacting relationship among genes", and an item correlated to a vertex corresponded to "a factor that changes expression of a gene" was used as an experimental target graph. Note that the total number of the above mentioned factors was 173 kinds. The numbers of vertexes and links in the experimental target graph were as follows:

the number of vertexes: 6152
the number of links: 3318

According to the method A, detection of the set C was completed in 35.9 seconds. Meanwhile, according to the method B, the memory ran short in 17302 seconds after the experiment started, and as a result, the process was forcibly terminated. This was considered because a huge number of frequent item set candidates were produced for detection of a frequent item set at the phase B1.

With reference to the above-described experimental results, it can be concluded that a memory amount and a time period necessary for the process were reduced according to the method A according to this embodiment, compared to the method B.

The invention claimed is:

1. A subgraph detection device, comprising:

graph data obtaining means for obtaining graph data indicating a graph including a plurality of vertexes and one or more edges;

vertex data obtaining means for obtaining vertex data that correlates an element set including at least one kind of element to the vertex; and subgraph detection means for carrying out detection, based on the graph data and the vertex data, of a subgraph being a subgraph of the graph in which a product set of the element sets correlated to the respective vertexes in the subgraph includes an N (N>=1) or larger number of kinds of elements, wherein the subgraph detection means includes:

determination means, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, for carrying out determination, when a vertex set of a node being the determination target includes a plurality of vertexes, to see whether or not a product set of element sets correlated to the respective vertexes in the vertex set includes the N or larger number of kinds of elements, and means for carrying out the detection, based on a result of determination by the determination means, and when a product set of element sets correlated to respective vertexes in a vertex set of a first node in the search tree is included in a product set of element sets correlated to respective vertexes in a vertex set of a second node that is a node having a vertex set including an end vertex that is same as an end vertex in the vertex set of the first node and that is a node having a vertex set including the vertex set of the first node, the determination means does not carry out the determination with respect to a vertex set of a descendant node of the first node as the determination target.

2. The subgraph detection device according to the claim 1, wherein the determination means, makes respective nodes of the search tree as a determination target in the search order according to the depth-first search algorithm, and the determination means, when a product set of element sets correlated to respective vertexes in a vertex set of the first node is included in a product set of element sets correlated to respective vertexes in a vertex set of the second node that is a node having a vertex set including an end vertex that is same as an end vertex in the vertex set of the first node and that is a node before the first node in the search order, does not carry out the determination with respect to a vertex set of a descendant node of the first node as the determination target.

3. The subgraph detection device according to claim 2, wherein the subgraph detection means includes means for storing, when the determination is carried out, the product set of the element sets correlated to the respective vertexes in the vertex set of the node being the determination target as a reference set in reference set storage means so as to be correlated to an end vertex in the vertex set of the node being the determination target, and when the product set of the element sets correlated to the respective vertexes in the vertex set of the first node is included in a reference set that is stored in the reference set storage means so as to be correlated to the end vertex in the vertex set of the first node, the determination means does not carry out the determination with respect to the vertex set of the descendant node of the first node as the determination target.

4. A subgraph detection device comprising:

graph data obtaining means for obtaining graph data indicating a graph including a plurality of vertexes and one or more edges;

vertex data obtaining means for obtaining vertex data that correlates an element set including at least one kind of element to the vertex; and subgraph detection means for carrying out detection, based on the graph data and the vertex data, of a subgraph being a subgraph of the graph in which a product set of the element sets correlated to the respective vertexes in the subgraph includes an N (N >=1) or larger number of kinds of elements, wherein the subgraph detection means includes:

determination means, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, for carrying out determination, when a vertex set of a node being the determination target includes a plurality of vertexes, to see whether or not a product set of element sets correlated to the respective vertexes in the vertex set includes the N or larger number of kinds of elements, and means for carrying out the detection, based on a result of determination by the determination means, and when a vertex set of a third node in the search tree includes only one vertex, and an element set correlated to the vertex is included in a product set of element sets correlated to respective vertexes in a vertex set of a fourth node that is a node having a vertex set including the vertex as an end vertex, the determination means does not carry out the determination with respect to a vertex set of a descendant node of the third node as the determination target.

5. The subgraph detection device according to the claim 4, wherein the determination means, makes respective nodes of the search tree as a determination target in the search order according to the depth-first search algorithm, the determination means, when a vertex set of the third node includes only one vertex, and an element set correlated to the vertex is included in a product set of element sets correlated to respective vertexes in a vertex set of the fourth node that is a node having a vertex set including the vertex as an end vertex and that is a node before the third node in the search order, does not carry out the determination with respect to a vertex set of a descendant node of the third node as the determination target.

6. The subgraph detection device according to claim 5, wherein the subgraph detection means includes:

means for storing, when the determination is carried out, the product set of the element sets correlated to the respective vertexes in the vertex set of the node being the determination target as a reference set in reference set storage means so as to be correlated to an end vertex in the vertex set of the node being the determination target, and when the vertex set of the third node includes only one vertex and the element set correlated to the vertex is included in a reference set that is stored in the reference set storage means so as to be correlated to the vertex, the determination means does not carry out the determination with respect to the vertex set of the descendant node of the third node as the determination target.

7. A subgraph detection device, comprising: p1 graph data obtaining means for obtaining graph data indicating a graph including a plurality of vertexes and one or more edges;

vertex data obtaining means for obtaining vertex data that correlates an element set including at least one kind of element to the vertex; and subgraph detection means for carrying out detection, based on the graph data and the vertex data, of a subgraph being a subgraph of the graph in which a product set of the element sets correlated to the respective vertexes in the subgraph includes an N (N >=1) or larger number of kinds of elements, wherein the subgraph detection means includes:

determination means, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, for carrying out determination, when a vertex set of a node being the determination target includes a plurality of vertexes, to see whether or not a product set of element sets correlated to the respective vertexes in the vertex set includes the N or larger number of kinds of elements, and means for carrying out the detection, based on a result of determination by the determination means, and when a product set of element sets correlated to respective vertexes in a vertex set of the node does not include the N or large number of kinds of elements, the determination means does not carry out the determination with respect to a vertex set of a descendant node of the node as the determination target.

8. A subgraph detection method, comprising:
a graph data obtaining step of obtaining graph data indicating a graph including a plurality of vertexes and one or more edges;
a vertex data obtaining step of obtaining vertex data that correlates an element set including at least one kind of element to the vertex; and
a subgraph detection step of carrying out detection, based on the graph data and the vertex data, of a subgraph being a subgraph of the graph in which a product set of the element sets correlated to the respective vertexes in the subgraph includes an N (N>=1) or larger number of kinds of elements,
wherein the subgraph detection step comprises:
a determination step that, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, of carrying out determination, when a vertex set of a node being the determination target includes a plurality of vertexes, to see whether or not a product set of element sets correlated to the respective vertexes in the vertex set includes the N or larger number of kinds of elements, and
a detection step of carrying out the detection, based on a result of determination by the determination step, and
when a product set of element sets correlated to respective vertexes in a vertex set of a first node in the search tree is included in a product set of element sets correlated to respective vertexes in a vertex set of a second node that is a node having a vertex set including an end vertex that is same as an end vertex in the vertex set of the first node and that is a node having a vertex set including the vertex set of the first node, the determination with respect to a vertex set of a descendant node of the first node as the determination target is not carried out by the determination step.

9. A non-transitory computer readable information recording medium recording a program for causing a computer to function as:
graph data obtaining means for obtaining graph data indicating a graph including a plurality of vertexes and one or more edges;
vertex data obtaining means for obtaining vertex data that correlates an element set including at least one kind of element to the vertex; and
subgraph detection means for carrying out detection, based on the graph data and the vertex data, of a subgraph being a subgraph of the graph in which a product set of the element sets correlated to the respective vertexes in the subgraph includes an N (N>=1) or larger number of kinds of elements,
wherein the subgraph detection means includes:
determination means, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, for carrying out determination, when a vertex set of a node being the determination target includes a plurality of vertexes, to see whether or not a product set of element sets correlated to the respective vertexes in the vertex set includes the N or larger number of kinds of elements, and
means for carrying out the detection, based on a result of determination by the determination means, and
when a product set of element sets correlated to respective vertexes in a vertex set of a first node in the search tree is included in a product set of element sets correlated to respective vertexes in a vertex set of a second node that is a node having a vertex set including an end vertex that is same as an end vertex in the vertex set of the first node and that is a node having a vertex set including the vertex set of the first node, the determination means does not carry out the determination with respect to a vertex set of a descendant node of the first node as the determination target.

10. A subgraph detection method, comprising:
a graph data obtaining step of obtaining graph data indicating a graph including a plurality of vertexes and one or more edges;
a vertex data obtaining step of obtaining vertex data that correlates an element set including at least one kind of element to the vertex; and
a subgraph detection step of carrying out detection, based on the graph data and the vertex data, of a subgraph being a subgraph of the graph in which a product set of the element sets correlated to the respective vertexes in the subgraph includes an N (N>=1) or larger number of kinds of elements,
wherein the subgraph detection step comprises:
a determination step that, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, of carrying out determination, when a vertex set of a node being the determination target includes a plurality of vertexes, to see whether or not a product set of element sets correlated to the respective vertexes in the vertex set includes the N or larger number of kinds of elements, and
a detection step of carrying out the detection, based on a result of determination by the determination step, and
when a vertex set of a third node in the search tree includes only one vertex, and an element set correlated to the vertex is included in a product set of element sets correlated to respective vertexes in a vertex set of a fourth node that is a node having a vertex set including the vertex as an end vertex, the determination with respect to a vertex set of a descendant node of the third node as the determination target is not carried out by the determination step.

11. A non-transitory computer readable information recording medium recording a program for causing a computer to function as:
graph data obtaining means for obtaining graph data indicating a graph including a plurality of vertexes and one or more edges;

vertex data obtaining means for obtaining vertex data that correlates an element set including at least one kind of element to the vertex; and subgraph detection means for carrying out detection, based on the graph data and the vertex data, of a subgraph being a subgraph of the graph in which a product set of the element sets correlated to the respective vertexes in the subgraph includes an N (N>=1) or larger number of kinds of elements, wherein the subgraph detection means includes:

determination means, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, for carrying out determination, when a vertex set of a node being the determination target includes a plurality of vertexes, to see whether or not a product set of element sets correlated to the respective vertexes in the vertex set includes the N or larger number of kinds of elements, and means for carrying out the detection, based on a result of determination by the determination means, and when a vertex set of a third node in the search tree includes only one vertex, and an element set correlated to the vertex is included in a product set of element sets correlated to respective vertexes in a vertex set of a fourth node that is a node having a vertex set including the vertex as an end vertex, the determination means does not carry out the determination with respect to a vertex set of a descendant node of the third node as the determination target.

12. A subgraph detection method, comprising:

a graph data obtaining step of obtaining graph data indicating a graph including a plurality of vertexes and one or more edges;

a vertex data obtaining step of obtaining vertex data that correlates an element set including at least one kind of element to the vertex; and a subgraph detection step of carrying out detection, based on the graph data and the vertex data, of a subgraph being a subgraph of the graph in which a product set of the element sets correlated to the respective vertexes in the subgraph includes an N (N >=1) or larger number of kinds of elements, wherein the subgraph detection step comprises:

a determination step that, while making respective nodes of a search tree as a determiation target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, of carrying out determination, when a vertex set of a node being the determination target includes a plurality of vertexes, to see whether or not a product set of element sets correlated to the respective vertexes in the vertex set includes the N or larger number of kinds of elements, and a detection step of carrying out the detection, based on a result of determination by the determination step, and when a product set of element sets correlated to respective vertexes in a vertex set of the node does not include the N or large number of kinds of elements, the determination with respect to a vertex set of a descendant node of the node as the determination target is not carried out by the determination step.

13. A non-transitory computer readable information recording medium recording a program for causing a computer to function as:

graph data obtaining means for obtaining graph data indicating a graph including a plurality of vertexes and one or more edges;

vertex data obtaining means for obtaining vertex data that correlates an element set including at least one kind of element to the vertex; and subgraph detection means for carrying out detection, based on the graph data and the vertex data, of a subgraph being a subgraph of the graph in which a product set of the element sets correlated to the respective vertexes in the subgraph includes an N (N >=1) or larger number of kinds of elements, wherein the subgraph detection means includes:

determination means, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, for carrying out determination, when a vertex set of a node being the determination target includes a plurality of vertexes, to see whether or not a product set of element sets correlated to the respective vertexes in the vertex set includes the N or larger number of kinds of elements, and means for carrying out the detection, based on a result of determination by the determination means, and when a product set of element sets correlated to respective vertexes in a vertex set of the node does not include the N or large number of kinds of elements, the determination means does not carry out the determination with respect to a vertex set of a descendant node of the node as the determination target.

14. A subgraph detection device comprising at least one microprocessor configured to:

obtain graph data indicating a graph including a plurality of vertexes and one or more edges;

obtain vertex data that correlates an element set including at least one kind of element to the vertex; and carry out detection, based on the graph data and the vertex data, of a subgraph being a subgraph of the graph in which a product set of the element sets correlated to the respective vertexes in the subgraph includes an N (N>=1) or larger number of kinds of elements, wherein the detection of the subgraph comprises:

the at least one microprocessor, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, carries out a determination, when a vertex set of a node being the determination target includes a plurality of vertexes, to see whether or not a product set of element sets correlated to the respective vertexes in the vertex set includes the N or larger number of kinds of elements, and the at least one microprocessor carries out the detection, based on a result of determination, and when a product set of element sets correlated to respective vertexes in a vertex set of a first node in the search tree is included in a product set of element sets correlated to respective vertexes in a vertex set of a second node that is a node having a vertex set including an end vertex that is same as an end vertex in the vertex set of the first node and that is a node having a vertex set including the vertex set of the first node, the at least one microprocessor does not carry out the determination with respect to a vertex set of a descendant node of the first node as the determination target.

15. A subgraph detection device, comprising at least one microprocessor configured to:

obtain graph data indicating a graph including a plurality of vertexes and one or more edges;

obtain vertex data that correlates an element set including at least one kind of element to the vertex; and carry out detection, based on the graph data and the vertex data, of a subgraph being a subgraph of the graph in which a product set of the element sets correlated to the respective vertexes in the subgraph includes an N (N>=1) or larger number of kinds of elements, wherein the detection of the subgraph comprises:

the at least one microprocessor, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, carries out determination, when a vertex set of a node being the determination target includes a plurality of vertexes, to see whether or not a product set of element sets correlated to the respective vertexes in the vertex set includes the N or larger number of kinds of elements, and the at least one microprocessor carries out the detection, based on a result of determination, and when a vertex set of a third node in the search tree includes only one vertex, and an element set correlated to the vertex is included in a product set of element sets correlated to respective vertexes in a vertex set of a fourth node that is a node having a vertex set including the vertex as an end vertex, the at least one microprocessor does not carry out the determination with respect to a vertex set of a descendant node of the third node as the determination target.

16. A subgraph detection device comprising at least one microprocessor configured to:

obtain graph data indicating a graph including a plurality of vertexes and one or more edges;

obtain vertex data that correlates an element set including at least one kind of element to the vertex; and carry out detection, based on the graph data and the vertex data, of a subgraph being a subgraph of the graph in which a product set of the element sets correlated to the respective vertexes in the subgraph includes an N (N>=1) or larger number of kinds of elements, wherein the detection of the subgraph comprises:

the at least one microprocessor, while making respective nodes of a search tree as a determination target in a search order according to a depth or width-first search algorithm, in which the nodes each have a set of vertexes in the graph, and the search tree has a vertex set obtained by adding, as a new end vertex, one vertex adjacent to an end vertex in a vertex set of a parent node to the vertex set as a child node of the parent node, carries out determination, when a vertex set of a node being the determination target includes a plurality of vertexes, to see whether or not a product set of element sets correlated to the respective vertexes in the vertex set includes the N or larger number of kinds of elements, and the at least one microprocessor carries out the detection, based on a result of determination, and when a product set of element sets correlated to respective vertexes in a vertex set of the node does not include the N or large number of kinds of elements, the at least one microprocessor does not carry out the determination with respect to a vertex set of a descendant node of the node as the determination target.

* * * * *